United States Patent [19]

Okamura et al.

[11] 4,368,203

[45] Jan. 11, 1983

[54] ANTIBIOTICS AND DERIVATIVES THEREOF HAVING β-LACTAMASE INHIBITORY ACTIVITY AND PRODUCTION THEREOF

[75] Inventors: Kazuhiko Okamura, Yamato; Shoji Hirata, Miyagi; Yasushi Okumura; Yasuo Fukagawa, both of Kamakura; Yasutaka Shimauchi, Ninomiya; Tomoyuki Ishikura, Chigasaki; Kageaki Kouno, Tokyo, all of Japan; Joseph Lein, Fayetteville, N.Y.

[73] Assignee: Sanraku-Ocean Co., Ltd., Tokyo, Japan

[21] Appl. No.: 949,854

[22] Filed: Oct. 10, 1978

[30] Foreign Application Priority Data

Oct. 13, 1977 [JP] Japan .................................. 52-121857
Dec. 29, 1977 [JP] Japan .................................. 52-160424

[51] Int. Cl.³ .................... C07D 487/04; A61K 31/40
[52] U.S. Cl. ........................... 424/274; 260/245.2 T; 435/119
[58] Field of Search .................... 260/326.31, 245.2 T; 429/274

[56] References Cited

U.S. PATENT DOCUMENTS 4,235,922  11/1980  Ratcliffe et al. ............. 260/245.2 T

OTHER PUBLICATIONS

Okamura et al.; Jour. of Antibiotics, vol. 31, No. 5 pp. 480-482, (5/78).

Primary Examiner—Mary C. Lee
Attorney, Agent, or Firm—Wenderoth, Lind & Ponack

[57] ABSTRACT

A novel antibiotic substance of the formula

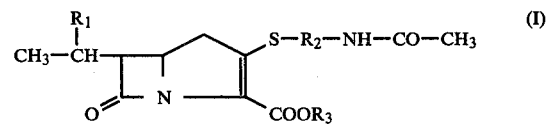

wherein $R_1$ is $CH_3$ and $R_2$ is $-CH_2-CH_2-$ or $R_1$ is H and $R_2$ is $-CH=CH-$; and $R_3$ represents hydrogen, lower alkyl or triphenylmethyl, and including the salts of the compound of formula (I) wherein $R_3$ is hydrogen, said antibiotic substance having strong antibiotic activity and β-lactamase inhibiting effect, and a method for producing the same by aerobic cultivation of Streptomyces A271.

9 Claims, 8 Drawing Figures

ANTIBIOTICS AND DERIVATIVES THEREOF HAVING β-LACTAMASE INHIBITORY ACTIVITY AND PRODUCTION THEREOF

BACKGROUND OF THE INVENTION

The present invention relates to new antibiotics, their preparation and to uses as antimicrobial agents.

Some antibiotics having β-lactamase inhibitory activity or β-lactamase inhibitory agents have so far been known. For example, the following have been reported: MC696-SY2-A and B isolated from the culture broth of a MC696-SY2-producing strain belonging to the genus Streptomyces (U.S. Pat. No 3,928,569 Derwent CPI 19171X), MM4550 or MM13902 isolated from a cultivation product of an MM4550 or MM13902 producing strain which belongs to the genus Streptomyces (German Appln. DOS No. 2,513,855: Derwent CPI 67721W; German Appln. DOS No. 2,513,854: Derwent CPI 67720W), clavulanic acid isolated from a cultivation product of *Streptomyces clavuligerus* (German Appln. DOS No. 2,517,316: Derwent CPI 72840W), and the like. The antibiotic thienamycin having a penicillin-like chemical skeleton and the derivatives thereof have also been reported (U.S. Pat. No. 3,950,357: Derwent CPI 31696X; German Appln. DOS No. 2,652,677: Derwent CPI 40282Y; Belgian Pat. No. 848,346: Derwent CPI 34505Y; Belgian Pat. No. 848,349: Derwent CPI 34507: German Appln. DOS No. 2,652,680: Derwent CPI 40283Y; German Appln. DOS No. 2,652,675: Derwent CPI 40280Y: German Application DOS No. 2,652,674: Derwent CPI 40279Y; German Appln. DOS No. 2,652,676: Derwent CPI 40281Y).

The present inventors discovered a novel antibiotic, β-lactam antibiotic "PS-5", of the following formula

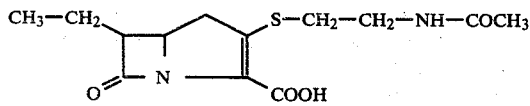

which is not described in the aforesaid prior literature references, and already disclosed it in Japanese Patent Applications Nos. 35375/77 and 94651/77.

SUMMARY OF THE INVENTION

This invention relates to new antibiotics and the derivatives thereof. More particularly, it is concerned with novel antibiotics defined as PS-6 and PS-7 and the derivatives thereof, which have strong antibiotic activity, β-lactamase inhibitory activity and ability to synergistically enhance the antibiotic activity of penicillins, cephalosporins or the like against β-lactamase producers. It also pertains to a method for producing these novel antibiotic substances, and to antibiotic compositions containing these substances.

The first object of the present invention is to provide new antibiotic substances PS-6 and PS-7 having both strong antibiotic activity and β-lactamase inhibitory activity.

The second object of the present invention is to provide ester derivatives, particularly the trityl derivative, of the antibioctics PS-6 and PS-7 which also show strong antibiotic activity and β-lactamase inhibitory activity.

Another object of this invention is to show that the new antibiotic PS-6 and PS-7 and the trityl derivative thereof, also have the ability to synergistically enhance the antibiotic activity of penicillins, cephalosporins or the like against β-lactamase-producing resistant bacteria.

Still another object of this invention is to provide methods for producing the antibiotics PS-6 and PS-7 by a fermentation process.

Yet another object of this invention is to provide methods for producing the derivatives of the antibiotics PS-6 and PS-7, and more particularly, the ester derivatives, above all, the trityl derivative.

A further object of this invention is to provide preventive and therapeutic methods and compositions of the antibiotics PS-6 and PS-7 or its trityl derivative for use in infectious diseases caused by Gram-positive and Gram-negative bacteria, including synergistic combinations with penicillins, cephalosporins and other β-lactamase sensitive antibiotics.

Other objectives of this invention will become apparent from the following description.

Figure 1:
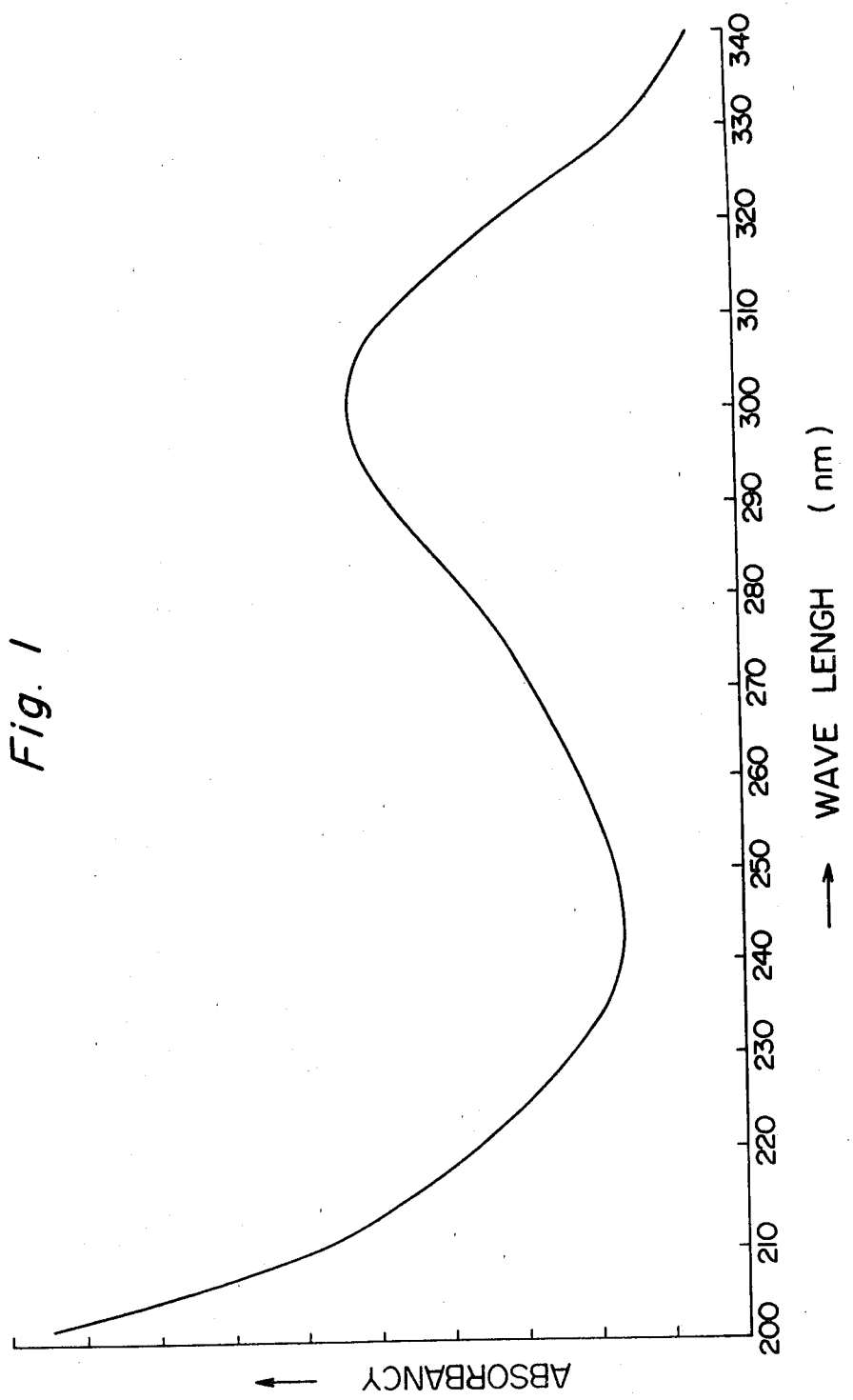
FIG. 1 is a spectrophotometer chart re antibiotic PS-6 sodium salt.

The present invention provides a compound of the formula

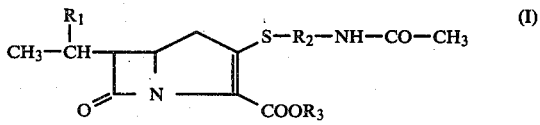

wherein $R_1$ is $CH_3$ and $R_2$ is $-CH_2-CH_2-$, or $R_1$ is H and $R_2$ is $-CH=CH-$; and $R_3$ represents hydrogen, lower alkyl or triphenylmethyl, and salts of the compound of formula (I) in which $R_3$ is hydrogen.

A compound of formula (I) in which $R_1$ is $CH_3$ and $R_2$ is $-CH_2-CH_2-$, i.e.

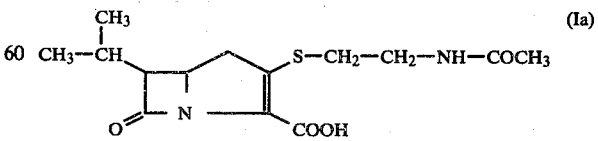

is called "antibiotic PS-6" in the present specification and the appended claims.

A compound of formula (I) in which $R_1$ is H, and $R_2$ is $-CH=CH-$, i.e.

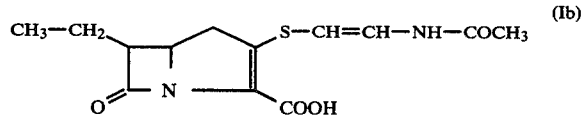 (Ib)

is called "antibiotic PS-7" in the present specification and the appended claims.

DETAILED DESCRIPTION OF THE INVENTION

These antibiotics PS-6 and PS-7 and their derivatives are described below in detail.

[I] Antibiotic PS-6

The antibiotic PS-6 is characterized by the following physico-chemical properties and biological properties:

Physico-chemical properties of antibiotic PS-6

(1) Paper chromatography

The antibiotic PS-6 (sodium salt) indicates the following $R_f$ values when descending paper chromatography is conducted with the use of Toyo Filter Paper No. 50 (Toyo Roshi Kaisha Ltd.) and the following solvents:
Acetonitrile/Tris/EDTA (Note 1): $R_f=0.41$
Ethanol/water (7/3): $R_f=0.65$
[Note 1: Mixed solvent composed of 120 ml of acetonitrile, 30 ml of 1/10 M tris(hydroxymethyl)-aminomethane-hydrochloric acid buffer (pH 7.5) and 1 ml of 1/10 M sodium ethylenediamine tetraacetate aqueous solution (pH 4.5).]

Solvent ratios in this specification are expressed as volume to volume unless otherwise mentioned.

(2) Thin layer chromatography (TLC)

The following $R_f$ values of antibiotic PS-6 (sodium salt) are obtained when thin layer chromatography is conducted with the use of Chromatogram Sheet 13254 Cellulose (No. 6065) (Trademark of Eastman Kodak Co., Ltd.) and the following developing solvents.
n-Butanol/ethanol/water (4/1/5) (Upper layer): $R_f=0.67$
n-Propanol/water (8/2): $R_f=0.69$
n-Butanol/i-Propanol/water(7/7/6): $R_f=0.70$
Acetonitrile/water (8/2): $R_f=0.63$ (3) High voltage paper electrophoresis The following behavior is observed in a buffer solution having the following composition and pH when the antibiotic PS-6 (sodium salt) is subjected to electrophoresis on Toyo Filter Paper No. 50 (Toyo Roshi Kaisha Ltd.) by using a high voltage paper electrophoresis apparatus (Savant Instrument Inc., High Voltage Power Supply HV 3000 A, Flat Place Electrophoresis Chamber FP 18A).

The antibiotic is seen to migrate through a distance of at least 5 mm, usually 10–40 mm toward the anode when passing a current for 30 minutes on a potential gradient of 42 V/cm in a buffer (pH 8.6) composed of 3000 ml water, 3.3 g barbital and 25.5 g sodium barbital.

(4) Behavior against β-lactamase

The activity is inactivated by β-lactamase of *Bacillus cereus.*

(5) Distinction among acid, neutral and base

Antibiotic PS-6 is a mono-basic acid having one carboxyl group in the molecule.

(6) UV absorption spectrum

Characteristic UV absorption maximum of antibiotic PS-6 (sodium salt) is as follows:

$\lambda_{max}^{H_2O}$ = approximately 300 nm (7) IR absorption spectrum

Characteristic IR absorption maxima of the antibiotic PS-6 (sodium salt) measured by KBr tablet method are as follows:
approximately 1760 cm$^{-1}$ (—CO— in β-lactam ring)
approximately 1660 cm$^{-1}$ (—CO— of amide)
approximately 1600 cm$^{-1}$ (—COO$^\ominus$)

(8) Proton NMR spectrum

Antibiotic PS-6 (sodium salt) indicated the following characteristic signals in 100 MHz proton NMR spectrum measured in heavy water (D$_2$O);

(i) A pair of doublets centered approximately at 0.94 and 0.98 ppm with coupling constants of approximately 7.0 Hz

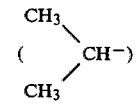

(ii) a sharp singlet approximately at 1.92 ppm (C$\underline{H}_3$—CO—)

(iii) a multiplet approximately at 2.40–3.50 ppm

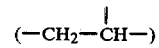

(iv) a multiplet approximately at 3.90–4.20 ppm

(9) Molecular weight

Approximately 312 (calculated from the results of high resolution mass spectrometry for the methyl ester of antibiotic PS-6)

(10) Color reaction
Ehrlich reagent reaction: positive
Iodine-chloroplatinic acid reaction: positive
Ninhydrin reaction: negative

(11) Solubility

The antibiotic PS-6 is soluble in water at pH 6 to 9, but substantially insoluble in benzene, acetone and ethylacetate.

The above physico-chemical properties clearly demonstrate that the groups

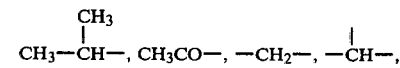
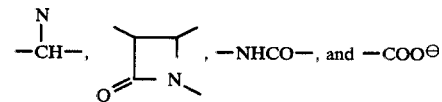

are present in the molecule of the antibiotic PS-6 (sodium salt).

The antibiotic PS-6 is assumed to have a thienamycin (see U.S. Pat. No. 3,950,357) skeleton including a sulfur side chain similar to the antibiotic PS-5 stated hereinbefore from its UV absorption maximum and the shift of UV absorption maximum from 300 nm to 316 nm as a result of the esterification of the antibiotic which will be discussed later. Further, the molecular formula of antibiotic PS-6 is calculated as $C_{14}H_{20}N_2O_4S$ from the results of the high resolution mass spectrometry for the methyl ester.

The above data lead to the belief that antibiotic PS-6 has the following structure:

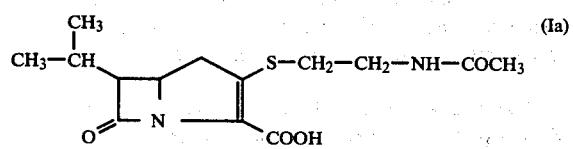

Biological properties of the antibiotic PS-6

(1) Antibiotic spectra

The antibiotic PS-6 having broad spectral antibiotic activities shows very strong activity against various bacteria, for example, Gram-positive bacteria belonging to the genera Staphylococcus, Diplococcus, Streptococcus, Bacillus, and the like, and Gram-negative bacteria belonging to the genera Alcaligenes, Comamonas, and the like. The antibiotic PS-6 also shows good activity against, for example, Gram-negative bacteria belonging to the genera Klebsiella, Proteus, and the like.

It is characteristic that the antibiotic PS-6 shows strong activity against Gram-negative bacteria which are resistant to antibiotics having $\beta$-lactam ring structure, for example, those bacteria which belong to the genera Citrobacter, Proteus, Klebsiella, and the like.

(2) Increasing of the antibiotic activity of other antibiotics against $\beta$-lactamase-producing bacteria The antibiotic PS-6 has the ability to increase the antibiotic activity of other antibiotics, especially $\beta$-lactam antibiotics such as penicillins and cephalosporins, against $\beta$-lactamase-producing bacteria such as *Proteus vulgaris, Serratia marcescens* and the like.

(3) Activity in vivo

The antibiotic showed a marked therapeutic effect when administered to mice infected with pathogenic Gram-positive bacteria.

(4) Toxicity

The antibiotic showed no toxicity when intraperitoneally administered to mice in a dose of 500 mg/kg.

[II] Antibiotics PS-7

Physico-chemical properties of the antibiotic PS-7

(1) Paper Chromatography

The antibiotic PS-7 (sodium salt) gives the following Rf values in descending paper chromatography on Toyo filter paper No. 50 (Toyo Roshi Co.) with the following solvent system:

Acetonitrile/Tris/EDTA: Rf=0.41
Ethanol/Water (7/3): Rf=0.68

(2) Thin-layer chromatography (TLC)

The antibiotic PS-7 (sodium salt) shows the following Rf values in TLC on a Chromagram sheet 13254 cellulose (No. 6065) (Eastman Kodak Co.) with the following solvent system:

n-Butanol/Ethanol/Water (4/1/5)(Upper layer): Rf=0.60
n-Propanol/Water (7/3): Rf=0.81
n-Butanol/Isopropanol/Water (7/7/6): Rf=0.71
Acetonitrile/Water (8/2): Rf=0.65

(3) High voltage paper electrophoresis

The following migration is observed with the antibiotic PS-7 (sodium salt) in electrophoresis on Toyo filter paper No. 50 (Toyo Roshi Co.) with a buffer solution of the following pH value using a High-Voltage-Paper-Electrophoresis Apparatus (Savant Instruments Co., High voltage power supply HV 3000 A, Electrophoresis vessel FP 18 A): The antibiotic PS-7 migrates toward the anode at least 5 mm, generally within the range between 10 and 40 mm in a buffer solution consisting of 3.3 g of barbital, 25.5 g of sodium barbital and 3000 ml of water (pH 8.6) when passing a current at 42 V/cm for 30 minutes.

(4) Behavior against $\beta$-lactamase

The antibiotic PS-7 is inactivated by $\beta$-lactamase from *Bacillus cereus*.

(5) Distinction among acid, neutral and base

The antibiotic PS-7 is a mono-basic acid containing one carboxyl group in the molecule.

(6) UV absorption spectrum

The ultraviolet absorption spectrum of the antibiotic PS-7 (sodium salt) has the following characteristic absorption maxima:

$\lambda_{max}^{H2O}$ = about 220 nm and
$\lambda_{max}^{H2O}$ = about 308 nm (7) IR absorption spectrum The infrared absorption spectrum of the antibiotic PS-7 (sodium salt) measured in a KBr tablet has characteristic absorption maxima at the following wave numbers:

About 1760 cm$^{-1}$ (—CO— of $\beta$-lactam ring)
About 1670 cm$^{-1}$ (—CO— of amide)
About 1620 cm$^{-1}$ (—COO$^\ominus$ and —CH=CH—)

(8) Proton NMR spectrum

In 100 MHz proton nuclear magnetic resonance spectrum in heavy water (D$_2$O), the antibiotic PS-7 (sodium salt) shows the following appearent characteristic signals:

(i) A triplet with a center at about 0.96 ppm

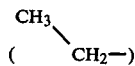

(ii) A multiplet with a center at about 1.72 ppm (—CH$_2$—CH$_3$)
(iii) A sharp singlet at about 2.05 ppm (CH$_3$—CO—)
(iv) A multiplet at about 2.96–3.38 ppm (—CH$_2$—CH—)
(v) A signal with a center at about 3.96 ppm

(vi) A pair of doublets centered at about 6.02 ppm and about 7.10 ppm (J=about 14 Hz) (—CH=CH—)

(9) Molecular weight

Approximately 296 (calculated from the results of high resolution mass spectrometry for the methyl ester of antibiotic PS-7)

(10) Color reaction

Ehrlich reagent reaction: Positive
Iodine-chloroplatinic acid reaction: Positive
Ninhydrin reaction: Negative

(11) Solubility

Soluble in water at pH 6–9; practically insoluble in benzene, acetone and ethyl acetate.

These physico-chemical properties lead to the confirmation that the antibiotic PS-7 (sodium salt) has the groups CH$_3$—CH$_2$—, CH$_3$CO—, —CH=CH—,

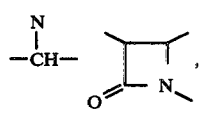

—NHCO— and —COO⊖ in the molecule. It is believed from these data that the antibiotic PS-7 provided by the present invention is a compound of the following structural formula:

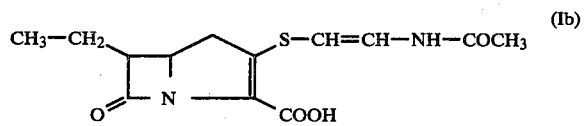

Biological properties of the antibiotic PS-7

(1) Antibiotic spectra

The antibiotic PS-7 has broad antimicrobial activity. It shows very high antimicrobial activity on various microorganisms, for example, Gram-positive bacteria belonging to genus Staphylococcus or genus Diplococcus, and it also has high antimicrobial activity on Gram-negative bacteria belonging to, for example, genus Alcaligenes.

In particular the antibiotic PS-7 is characterized by its high antimicrobial activity on the Gram-negative bacteria belonging to, for example, genus Citrobacter or genus Enterobacter which are resistant to the known β-lactam antibiotics.

(2) Increasing of the antibiotic activity of other antibiotics against β-lactamase-producing bacteria The antibiotic PS-7 has the ability to enhance antimicrobial activity of other antibiotics, for example, β-lactam antibiotics such as cephalosporins on the β-lactamase-producing bacteria such as *Proteus vulgaris* or *Serratia marcescens*.

(3) Activity in vivo

The antibiotic showed a marked therapeutic effect when administered to mice infected with pathogenic Gram-positive bacteria.

(4) Toxicity

The antibiotic showed no acute toxicity when intraperitoneally administered to mice at a dose of 500 mg/kg.

According to this invention, the antibiotics PS-6 and/or PS-7 having the above-mentioned characteristic properties can be produced by a process which comprises cultivating microorganisms capable of producing antibiotics PS-6 and/or PS-7 in a nutrient medium and isolating the antibiotics PS-6 and/or PS-7.

Microorganisms capable of producing antibiotics PS-6 and PS-7 which can be used in this invention have the ability to produce either one or both of PS-6 and PS-7.

Typical microorganisms capable of producing antibiotics PS-6 and PS-7 belong to the genus Streptomyces. An example of the most suitable strain of the genus Streptomyces is a strain isolated from the soil sample collected near Eiheiji Temple in the Yoshida District of Fukui Prefecture, Japan and named strain No. A271. This strain has the ability to produce both antibiotics PS-6 and PS-7, and is preferred for use in this invention.

Taxonomical characteristics of Strain A271

The taxonomical characteristics of strain Streptomyces A271 are as follows:

(1) Morphological characteristics

Branching of sporulated aerial mycelium: Simply branched. Form of sporulated aerial mycelium: Top of aerial mycelium shows hooks, loops or incomplete spirals.

This is considered to belong to the Section Retinaculum-Apertum. These forms are particularly observed when the strain is cultivated on an oatmeal agar medium and a glycerin-asparagine agar medium, while a straight or flexuous form is occasionally observed on yeast extract-malt extract agar medium. Form and number in chain of spores: Oval or cylindrical spores forming a chain of more than 10 (usually 10 to 50) spores. Size and surface structure of spores: $0.8-1.0 \times 1.0-1.8\mu$, smooth surface. Neither flagella nor sporangium has been observed. Hyphae are formed on aerial mycelium.

(2) Cultural characteristics

Cultural characteristics of the strain A271 are shown in Table 1, in which the results of observation after 2 weeks cultivation at 28° C. are shown unless noted otherwise. The description of color is mainly based on the method of H. D. Tresner and E. J. Backus' "System of Color Wheels for Streptomycete Taxonomy", (see Appl. Microbiol. 11, 335, 1963) and the color code in "Guide to Color Standard" published by Japan Color Institute Foundation.

TABLE 1

| Media | Growth | Color of Aerial Mycelium | Color of Substrate Mycelium | Soluble Pigment |
|---|---|---|---|---|
| Sucrose-nitrate agar medium | abundant | light orange yellow (3ea) | light yellow (2fb) to light orange yellow (3ea) | none |
| Glucose-asparagine agar medium | abundant | pale orange yellow (3ca) to light orange yellow (3ea) | light yellow (1 2/1 fb)-2fb) | none |
| Glycerin-asparagine agar medium | abundant | pale orange yellow (3ca) to light orange yellow (3ea) | light yellow (2fb) to somewhat yellowish pink (4gc) | none |
| Starch inorganic salt agar medium | abundant | pale orange yellow (3ca) to light orange yellow (3ea) | light orange yellow (3ea) to light yellow (2fb) | none |
| Tyrosine agar medium | abundant | pale orange yellow (3ca) to light orange yellow (3ea) | light orange yellow (3ea) to brownish yellow | none |
| Nutrient agar medium | abundant | hardly formed; if formed, somewhat dark | pale yellow (2db) | none |
| Yeast extract-malt extract agar medium | abundant | pale orange yellow (3ca) to light orange yellow (3ea) | light orange yellow (3ea) to pale brown (4ie) | none |
| Oatmeal agar medium | abundant | pale orange (3ca) to light orange yellow (3ea) | light yellow (2fb) | none |

(3) Physiological characteristics (1) Growth temperature range: 10°–40° C., optimum 20°–30° C.

(2) Liquefaction of gelatin (on glucose-peptone-gelatin medium): liquefied (cultured at 20° C.)

(3) Hydrolysis of starch (on starch inorganic salt agar medium): hydrolyzed (4) Coagulation and peptonization of skimmed milk: peptonized but no coagulation observed (5) Formation of melanoid pigment: no melanoid pigment formed on tyrosine agar medium and peptone yeast ion agar medium and in tryptone-yeast extract broth (6) Utilization of the following various carbon sources (Pridham and Gottlieb agar medium):

|   |   |
|---|---|
| L-Arabinose | + |
| D-Xylose | + |
| D-Glucose | + |
| D-Fructose | − |
| Sucrose | ± |
| Inositol | − |
| L-Rhamnose | + |
| Raffinose | − |
| D-Mannitol | − |

(+ : well utilized,
± : slightly utilized,
− : very slightly utilized or not at all).

It is obvious from the above characteristics that the strain A271 belongs to the genus Streptomyces and shows characteristics shared by microorganisms belonging to Section RA, since the color of the mycelium surface is yellow or red, the spore surface is smooth and no water soluble pigment-like melanoid pigment is formed. Cultures having such taxonomical characteristics were looked for in Waksman's "The Actinomycetes" vol. 2" (1961), E. B. Shirling and D. Gottlieb's papers in International Journal of Systematic Bacteriology vol. 18, page 69-189 (1968), ibid., page 279-892 (1968), ibid., vol. 19, page 391-512 (1969), ibid., vol. 22, page 265-394 (1972), and Bargey's Manual of Determinative Bacteriology, 8th edition (1974). Similar cultures belonging to Section RA were found to be *Actinomyces cremeus, Actinomyces flavidovirens, Actinomyces albohelvatus, Actinomyces flavescens, Streptomyces rutgersensis, Streptomyces chryseus, Streptomyces helvaticus*. As one of the resembling cultures *Streptomyces pluricolorescens* was also selected, based on its morphological characteristics although it belongs to the Section RF. These 8 cultures except the last *Streptomyces pluricolorscens* were reported to produce aerial mycelium having a straight form or loops, the variation being dependent on the cultural conditions. Type cultures of the above 8 species were compared with the strain A271 of this invention after cultivation under the same conditions. Consequently, strain A271 has been found to be clearly different from these cultures in growth, the color of aerial mycelium, the color of substrate mycelium, and the utilization of carbon sources.

Table 2, 3 and 4 give the results of the comparison of strain A271 with the two cultures most closely resembling it.

TABLE 2

Comparison with the resembling cultures
Color of aerial *mycelium*

| Media | Strain A271 | Actinomyces cremeus ISP 5147 | Actinomyces flavidovirens ISP 5150 |
|---|---|---|---|
| Sucrose | light orange | hardly formed | not formed |
| nitrate agar medium | yellow | (3ea) | |
| Glucrose-asparagine agar medium | pale orange yellow (3ca) to light orange yellow (3ea) | pale orange yellow (3ca) | white (b) |
| Glycerin-asparagine agar medium | pale orange yellow (3ca) to light orange yellow (3ea) | pale orange yellow (3ca) | hardly formed; if formed slightly, white (a) |
| Starch inorganic agar medium | pale orange yellow (3ca) to light orange yellow (3ea) | pale orange yellow (3ca) | thinly formed white (a) to pale yellow (2db) |
| Nutrient agar medium | hardly formed, if formed somewhat dark | white (a) to pale orange yellow (3ca) | white |
| Yeast extract-malt extract agar medium | pale orange yellow (3ca) to light orange yellow (3ea) | pale yellow (2db) | white (b) to pale yellowish green (1cb) |
| Oatmeal agar medium | pale orange yellow (3ca) to light orange yellow (3ea) | white (b) to pale orange yellow (3ca) | white (b) to pale yellowish green (1bd) |

TABLE 3

Comparison with the resembling cultures
Color of substrate *mycelium*

| Media | Strain A271 | Actinomyces cremeus ISP 5147 | Actinomyces flavidovirens ISP 5150 |
|---|---|---|---|
| Sucrose-nitrate agar medium | light yellow (2fb) to light orange yellow (3ea) | poor growth colorless to white (b) | poor growth colorless to white (a) |
| Glucose-asparagine agar medium | light yellow (1 2/1 fb - 2fb) | light orange yellow (3ea) | pale yellow (2db) |
| Glycerin-asparagine agar medium | light yellow (2fb) to somewhat yellowish pink (4gc) | light orange yellow (3ea) | grayish yellow (3ec) |
| Starch-inorganic salt agar medium | light orange yellow (3ea) to light yellow (2fb) | moderate yellowish pink (4ea) | light yellow (2fb) |
| Tyrosine agar medium | light orange yellow (3ea) to brownish yellow | pale brown (4ie) | grayish yellow (3ec) |
| Nutrient agar medium | pale yellow (2db) | light orange yellow (3ea) | pale yellow (2db) |
| Yeast extract-malt extract agar medium | light orange yellow (3ea) to pale brown (4ie) | light orange yellow (3ea) to dark yellow | dull yellow |
| Oatmeal agar medium | light yellow (2fb) | somewhat yellowish pink (4gc) | pale yellow (2db) to pale orange yellow (3ca) |

TABLE 4

Comparison with the resembling cultures
Utilization of carbon sources

| Carbon Sources | Strain A271 | Actinomyces cremeus ISP 5147 | Actinomyces flavidovirens ISP 5150 |
|---|---|---|---|
| L-Arabinose | + | + | + |
| D-xylose | + | + | + |
| D-Glucose | + | + | + |
| D-Fructose | − | + | + |
| Sucrose | ± | − | − |
| Inositol | − | − | + |
| L-Rhamnose | + | − | + |
| Raffinose | − | − | − |
| D-Mannitol | − | − | − |

The following conclusion can be drawn from the results shown in the above Tables. Concerning the color of aerial mycelium, *Actinomyces flavidorvirens* is generally white but when it is yellow, it is greenish yellow, thus showing a clear difference from the strain A271 of this invention. *Actinomyces cremeus* generally shows a weaker reddish tone of pale orange yellow color than the strain A271, and therefore, is clearly distinguished from the Strain A271.

Concerning the color of substrate mycelium, *Actinomyces flavidovirens* shows pale yellow color and *Actinomyces cremeus* shows light orange yellow color in many cases, while the Strain A271 generally shows light yellow color. Furthermore, a detailed comparison of the experimental results obtained in various media shows that the Strain A271 is different from the other two cultures. The strain A271 differs from *Actinomyces cremeus* in the utilization of D-fructose and L-rhamnose and from *Actinomyces flavidovirens* in the utilization of D-fructose and inositol.

Accordingly, the strain A271 of this invention is clearly different from the two known cultures most closely resembling it. Consequently, the strain A271 is different from all known Streptomycetes species and is recognized as a new species, which is designated as Streptomyces sp. A271. This culture has been deposited with Fermentation Research Institute, Agency of Industrial Science and Technology, Japan where it has been assigned the culture number FERM-P No. 3984. A sample of the Streptomyces sp. A271 was also deposited with ATCC where it has been assigned the collection No. 31358. The microorganism Streptomyces sp. A-271 is also on deposit with the United States Department of Agriculture, Northern Regional Research Center as NRRL 12587.

In this invention, not only the Strain A271 itself but also the natural mutants and artificial mutants thereof which may be induced by chemical or physical treatments can be used.

The antibiotics PS-6 and/or PS-7 producers can be selected from a wide range of microorganisms which are not limited to a particular genus.

Selection of the microorganisms producing PS-6 and/or PS-7 can be carried out by the following method by a person who is skilled in the art.

Cultured broth filtrates of microorganisms isolated from soil are analyzed by using a bioassay agar plate inoculated with a β-lactam susceptible microorganism and another bioassay agar plate containing β-lactamase and inoculated with the same organism. The microorganisms giving broth filtrates which show smaller inhibitory zones on the latter bioassay plate than that on the former bioassay plate are selected for further work.

Then, the active components in the cultured broth of the microorganisms selected by the above method are adsorbed on activated carbon and then eluted. The concentrated eluates are developed by paper chromatography or thin layer chromatography which are followed by bioautography with a β-lactam susceptible microorganism as the assay organism. The screening method is more specifically described by the following example.

The Comamonas bioassay plate which will be described later is employed as the bioassay agar plate inoculated with β-lactam susceptible assay organism. The Comamonas CV bioassay plate and Comamonas CM bioassay plate are prepared by adding to the above Comamonas bioassay plate the β-lactamase produced by *Proteus vulgaris* P-5 and *Citrobacter freundii* E-9 respectively. Pulp discs of 8 mm diameter to which the cultured broth filtrates of microorganisms isolated from soil have been added are placed on the above bioassay plates and the plates are incubated at 35° C. for 20 hours.

After the incubation, the microorganisms whose broth filtrate give an inhibitory zone on the Comamonas bioassay plate and a smaller inhibitory zone on the Comamonas CV bioassay plate or the Comamonas CM bioassay plate are chosen.

To the broth filtrates of those microorganisms, 2% (W/V) of activated carbon ("Tokusei Shirasagi", Takeda Chemical Industries, Ltd.) is added and after stirring for 15 minutes, the insoluble material is collected by centrifugation. The insoluble material is washed with distilled water of the same volume as the broth filtrate used, and collected again by centrifugation. The washed insoluble material is eluted by adding 50% (V/V) aqueous acetone of a half volume of the broth filtrate used and stirring at room temperature for 30 min. After centrifugation, the supernatant is evaporated at 30° C.–35° C. by using a rotary evaporator to obtain a 20-fold concentrated solution as compared with the broth filtrate used. The concentrated solution is subjected to descending paper chromatography with filter paper (Toyo Filter Paper, Toyo Roshi Kaisha Ltd.) by developing for 16 hours with 80% acetonitrile/Tris EDTA solvent (composed of 120 ml acetonitrile, 30 ml pH 7.5 1/10 M tris-(hydroxymethyl)aminomethane-HCl buffer, and 1 ml sodium ethylenediaminetetraacetate aqueous solution). This is followed by bioautography with *Comamonas terrigena* B-996 as the assay organism.

The microorganisms isolated from soil whose biologically active product gives an inhibitory zone at the same migration distance (or the same Rf value) as that of antibiotic PS-5 are selected as candidates for antibiotic PS-5 productions. Selected candidate microorganisms are further examined to confirm the antibiotic PS-5 producing ability by additional paper and thin layer chromatography studies.

By using the above mentioned methods, a person who is skilled in the art can select other antibiotics PS-6 and/or PS-7 producers beside the strain Streptomyces sp. A271 previously described.

According to an embodiment of this invention the antibiotic PS-6 and/or PS-7 may be produced by inoculating spores of the mycelium of a microbial strain capable of producing said antibiotics such as Streptomyces sp. A271 into a nutrient medium and cultivating it aerobically.

Many nutrient sources generally utilized by Streptomycetes, for example carbohydrates, nitrogen sources, and inorganic salts can be used. Examples of the carbon sources are carbohydrates such as glucose, glycerin, maltose, sucrose, molasses, dextrin and starch, and oils and fats such as soybean oil, peanut oil or lard. Examples of the nitrogen sources are peptone, meat extract, soybean meal, cotton seed oil, dried yeast, corn steep liquor, yeast extract, skimmed milk, casein, sodium nitrate, ammonium nitrate and ammonium sulfate. Examples of the inorganic salts are dipotassium phosphate, sodium chloride, calcium carbonate and magnesium sulfate. Traces of metals such as cobalt or magnanese may be added if desired. Also usable are all nutrients which can be utilized by the organisms to produce the antibiotic PS-6 and/or PS-7. To prevent foaming during heat sterilization and fermentation, anti-foaming agents such as silicone oils and vegetable oils may be added.

The proportions of the nutrient sources described above are not particularly restricted, and can be varied over a wide range. Any one skilled in the art would be able to determine easily by simple small-scale experiments the optimal compositions and amounts of nutrient sources for a particular strain having the ability to produce the antibiotic PS-6 and PS-7 substances.

The present inventors found that the amount of antibiotic PS-6 accumulated can be increased by the addition of an amino acid or an organic acid to the culture medium during the cultivation of Streptomyces sp. A271. As the amino acid, neutral amino acids having 2 to 10 carbon atoms, especially valine and leucine, may be employed, and as the organic acid, aliphatic organic acids having 2 to 10 carbon atoms, especially n-valeric acid may be used. Amino acids of L-, D- and DL-forms can all be used, but the L-amino acids are most preferred. The amounts of these amino acids or organic acid to be added are not critical, but generally, they are preferable 0.01% to 1% (w/v), and most preferably from 0.1 to 0.5% (w/v), based on the culture broth. The time of addition is not limited. These compounds can be added to the medium at any time during cultivation. Preferably, however, they are added at the beginning of cultivation or within 100 hours after cultivation has begun. The amino acid or organic acid can be added at one time, or divided and fed at different intervals.

The medium may be sterilized prior to the cultivation. The pH of the medium is advantageously adjusted to a range of 4 to 9, particularly a range of 6 to 8 before or after the sterilization.

Cultivation of the antibiotic PS-6 and/or PS-7 producing strains can be carried out principally by a method similar to those which are generally employed in the production of antibiotics by streptomycetes. Cultivation under aerobic conditions is generally preferred. Usually, cultivation can be carried out with stirring and/or aeration. Although any cultivation method among stationary culture, shaking culture, and submerge culture involving aeration and stirring is employable, the submerge culture is advantageous. Employable fermentation temperatures are not particularly limited and may be in the range in which the growth of strains having the ability to produce antibiotics PS-6 and/or PS-7 is not substantially inhibited, and the antibiotics PS-6 and/or PS-7 can be produced. Although the fermentation temperature may be changed with the kind of producer strain used, the suitable temperature is generally in the range of 20° to 40° C., preferably 25° to 35° C.

The pH of the culture broth may be adjusted during fermentation to the range of 4 to 9, particularly 6 to 8, if desired, to conduct the fermentation favorably. In large-scale fermentation, it is preferred to cultivate a seed strain and inoculate the seed culture into the nutrient medium where it is cultivated by a submerge culture.

The fermentation may usually be continued until sufficient amounts of the antibiotics PS-6 and/or PS-7 are accumulated. The fermentation time is usually in the range of 30 to 90 hours but it varies with the composition of the medium, the fermentation temperature, the kind of the producer strain, etc.

Any person skilled in the art would be able to determine easily the optimum cultivating conditions by performing simple experiments according to the characteristics of a particular strain having the ability to produce the desired antibiotics. The amount of the antibiotic PS-6 and/or PS-7 accumulated in the fermentation broth can be determined by a bioassay method and bioautography which will be described hereinbelow.

Because the accumulated antibiotics PS-6 and/or PS-7 in the fermentation product are water-soluble and present mainly out of the microbical cells, it is preferred to remove the cells after fermentation by a known separating process such as filtration, centrifugation or extraction, and to recover the antibiotics from the filtrate, supernatant, or extract.

Recovery of the antibiotics may be conducted by various known processes. Particularly, those frequently employed for recovering carboxylic acid type antibiotics can be advantageously applied. For example, the following methods are used either alone or in combination, and at times repeatedly. Extraction at low pH with a solvent such as ethyl acetate, or n-butanol, and back extraction from the solvent layer into an aqueous layer at a higher pH; extraction at neutral pH with a solvent such as methylene chloride or chloroform in the presence of a lipophilic quaternary ammonium salt such as benzalkonium chloride or tetra n-butyl ammonium hydrogen sulfate, or a crown compound such as NISSO Crown ether dicyclohexyl-18-crown-6, NISSO Crown ether 15-crown-5 (Nippon Soda Co., Ltd.), and back extraction from the solvent layer into a neutral aqueous layer containing sodium iodide, potassium iodide or the like; adsorption on activated carbon, Amberlite XAD (Rohm & Hass Co.), Diaion HP-20 (Mitsubishi Chemical Industries Ltd.) or the like and elution with aqueous methanol solution, aqueous acetone solution or the like; adsorption and elution with ion exchange resin such as Dowex 1×2 (Dow Chemical Co.) or QAE-Sephadex A-25 (Pharmacia Fine Chemicals AB); gel filtration with Sephadex G-10 (Pharmacia Fine Chemicals AB), Bio-Gel P-2 (Bio-Rad Laboratories), Bio-Beads S-X3 (Bio-Rad Laboratories) or the like; column or thin layer chromatography with cellulose, Avicel SF (American Viscose Corp.), DEAE-Cellulose, Whatman DE-32 (Whatman Ltd.), DEAE-Sephadex A-25 (Pharmacia Fine Chemicals AB), silica gel, alumina, or the like; and forced precipitation by adding a solvent such as acetone.

In particular, for separation of the antibiotic PS-7 from analogue components having a saturated carbon chain of the sulfur side chain, such as the antibiotics PS-5 and PS-6, which may be produced and accumulated simultaneously, it is advantageous to employ the following method. The analogues having a saturated carbon chain are separated by usual anion exchange resin chromatography in which the active components are adsorbed on a polystyrene-type anion exchange resin such as Dowex 1×2 (Dow Chemicals Co.), Duolite A-101 (Chemical Process Co.), Amberlite 400 (Rohm and Haas Co.) or Diaion PA 306 (Mitsubishi Chemical Industries Ltd.) and the analogues are eluted with an aqueous inorganic salt, followed by eluting the antibiotics PS-7 with an aqueous solution of a polar solvent such as methanol or acetone (concentration: 1 to 80%, preferably 10 to 75%) containing 0.1 to 10%, preferably 1 to 5%, of an inorganic salt such as sodium chloride, potassium chloride, calcium chloride or sodium bromide.

The present inventors have also found that depending upon the cultivating conditions, a compound of the following formula

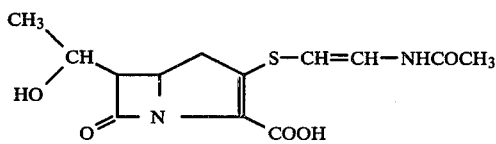

which we call antibiotic PS-4, or its salt is formed simultaneously in the fermentation broth. Accordingly, when the antibiotics PS-4 and PS-7 are produced simultaneously, they can be separated from each other by performing the various methods described above either in combination or repeatedly. It is particularly advantageous to employ the following process. A solution containing the antibiotics PS-4 and PS-7 is adsorbed on an adsorbent resin such as Dianion HP-20AG (Mitsubishi Chemical Industries Ltd.) and the antibiotics are eluted with a gradient from 0 to 50% and preferably 0 to 10% polar solvent dissolved in water such as aqueous acetone solution.

The behaviors of the antibiotics PS-6 and/or PS-7 in the recovery and isolation processes can be recognized by determining the antibiotics PS-6 and/or PS-7 by a bioassay method and bioautography which will be described later.

In the above indicated manner, one can obtain the antibiotics PS-6 and/or PS-7 having the above-described characteristics. Since the antibiotics PS-6 and PS-7 are somewhat labile as described above, the recovery and isolation processes must be conducted with great care.

Because antibiotics PS-6 and PS-7 tend in general to be more stable in the salt form than in the free acid state, the salt form is preferable in pharmaceutical use which will be described later, or when employed as an intermediate for synthesizing derivatives, or when put to the aforesaid purifying procedures.

The salt form described above includes, for example, alkali metal salts such as a sodium salt, potassium salt, or lithium salt; alkaline earth metal salts such as a calcium salt or magnesium salt; other metal salts such as an aluminum salt; an ammonium salt; salts with primary, secondary or tertiary amines such as monoethylamine, dimethylamine, triethylamine, monoethanolamine, or diethanolamine; and salts with organic bases such as benzathine or procaine. Suitable salts are pharmaceutically acceptable salts. Particularly suitable salts are alkali metal salts such as a sodium or potassium salt.

As described above, antibiotics PS-6 and PS-7 of this invention are monobasic acids having a carboxyl group in the molecule. Various esters can be derived from the antibiotics with various alcohols, mercaptans or derivatives thereof in the same manner as in the case of the known antibiotic, clavulanic acid or thienamycin, for example. Therefore, the invention also covers these esters.

Suitable esters of antibiotics PS-6 and PS-7 in this invention are those having the following structure:

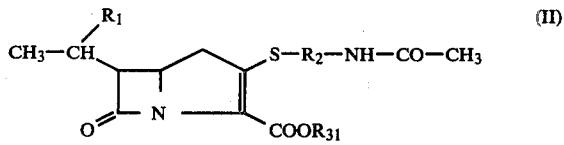

wherein $R_{31}$ represents a lower alkyl group or triphenylmethyl group, and $R_1$ and $R_2$ have the same meaning of the above, In the above formula (II), the lower alkyl group may be a straight-chain or branched-chain group, particularly a group having 6 or less carbon atoms, and more particularly a group having 1 to 4 carbon atoms. Examples are methyl, ethyl, n-propyl, iso-propyl, n-butyl, iso-butyl, n-pentyl, iso-pentyl, and n-hexyl.

According to this invention, the esters of the above formula (II) can be produced by reacting the compound (i.e. the antibiotic PS-6 or PS-7) of formula (I) or the salts thereof with compounds of general formula (III)

wherein, $R_{31}$ has the same meaning of the above and
  Y indicates an atom or group that can be cleaved off,
or with lower diazoalkanes.

As to the cleaving-off atom or group, Y in general formula (III), employable is any kind of atom or group which can be cleaved off when brought into contact with the carboxyl group of the antibiotic PS-6 or PS-7, for example, a halogen atom such as chlorine, bromine, or iodine, a hydroxyl group, a thiol group, a sulfonyloxy group, —COH, a reactive carbonyloxy group such as —O—CO—CF$_3$, or the like. Halogen atoms are particularly preferable.

Representative examples of the compound of general formula (III) are as follows:

Methyl alcohol, methyl iodide, dimethyl sulfonate, methyl mercaptane, ethanol, ethyl bromide, ethyl iodide, ethyl mercaptan, n-propyl chloride, n-propyl iodide, propyl alcohol, iso-propyl alcohol, iso-propyl bromide, iso-propyl iodide, n-butyl alcohol, n-butyl bromide, n-butyl iodide, n-pentyl alcohol, n-pentyl chloride, n-pentyl bromide, n-pentyl iodide, n-hexyl alcohol, n-hexyl bromide, n-hexyl iodide, trityl alcohol, trityl mercaptan, trityl chloride, and trityl bromide.

One of the representative examples of the lower diazoalkane is diazomethane.

The reaction of the antibiotic PS-6 or PS-7 with the compounds of general formula (III) or with the lower diazoalkane can be carried out by known methods for esterification. For example, the reaction of the antibiotic PS-6 or PS-7 with the compounds of general formula (III) or with the lower diazoalkanes can be carried out generally in the absence of a reaction medium. Generally, however, it is carried out in an inert liquid medium. Inert liquid media that can be used include, for example, hydrocarbons such as benzene, toluene, n-hexane or cyclohexane; halogenated hydrocarbons such as chloroform or methylene chloride; amides such as dimethyl formamide or hexamethylphosphoric triamide; dimethyl sulfoxide; ethers such as diethyl ether, diisopropyl ether, di n-butyl ether, tetrahydrofuran, or dioxane; esters such as ethyl acetate, or n-butyl acetate; and ketones such as acetone, or methyl ethyl ketone. These solvents can be used singly or as a mixture of two or more.

The reaction temperature is not critical and can be changed broadly depending upon the kind of the compound of general formula (III), the kind of the lower diazoalkane, the kind of liquid medium, etc. The reaction temperature can be selected from those at which the antibiotic PS-6 or PS-7 is not markedly decomposed. In general, the suitable temperature is not more than 60° C., preferably in the range between 0° C. and 40° C., and more preferably in the range between 5° C. and room temperature. As required, a reaction promotor such as trimethylamine, triethylamine, pyridine, or dicyclohexylcarbodiimide may be used in the reaction.

Under these conditions, the reaction can be terminated within about 1 to 24 hours, usually 3 to 12 hours.

The antibiotic substance PS-6 or PS-7 to be reacted with the compound of formula (III) or the lower diazoalkane needs not to be an isolated product alone. It may be culture broth of the antibiotic PS-6 or PS-7 producing strain, or a filtration broth left after the separation of the microbial cells from the culture broth. Or a crude antibiotic PS-6 or PS-7 obtained by at least partially purifying the cultivation product by the methods described hereinabove can also be used. Examples of such a partially purified product include a concentrated eluate from activated carbon with which the filtered broth has been treated; a concentrated eluate from Diaion HP-20 (Mitsubishi Chemical Industries Ltd.) to which the filtered broth has been subjected; a desalted concentrate with activated carbon of an eluate obtained with gradient concentration of sodium chloride in phosphate buffer from QAE-Sephadex (Pharmacia Fine Chemicals) on which the concentrated eluate from Dianion HP-20 has been adsorbed; a concentrated extract with methylene chloride in the presence of benzalkonium chloride; a concentrated extract with chloroform in the presence of crown compounds; and a concentrated extract with butanol at pH 3.5 at low temperature.

The ester of antibiotic PS-6 or PS-7 thus obtained can be isolated from the reaction mixture or or purified by methods known per se. For example, after the reaction has been completed, the reaction mixture is first poured into an aqueous medium to remove water-soluble impurities such as by-products. It is preferred to use a neutral buffer as the aqueous medium to keep the pH close to neutral. The ester of antibiotic PS-6 or PS-7 in this mixture is then extracted with a less polar organic solvent which is substantially water-immiscible, such as ethyl acetate, benzene or chloroform. A salt such as sodium chloride, or ammonium sulfate may be added to enhance the extraction efficiency by the salting-out effect.

After drying with anhydrous sodium sulfate, the ester can be isolated from the solvent layer by a method known per se, for example, gel filtration using Bio-Beads S-$X_3$ (Bio-Rad Laboratories), or Sephadex LH-20 (Pharmacia Fine Chemicals AB); or adsorption chromatography using a carrier such as silica gel, alumina, or Florisil (Floridin Co.), which can be used in some adequate combination and used repeatedly, if necessary.

The ester thus purified can be further purified by recrystallization from a solvent such as benzene, toulene, xylene, ethyl acetate, diethyl ether, methylene chloride, chloroform, hexane, and petroleum ether (boiling point range 30°–60° C.) either singly or a mixture.

Among the esters of general formula (II) which can be produced by the above processes, the antibiotic PS-6 or PS-7 trityl ester having formula (II-a)

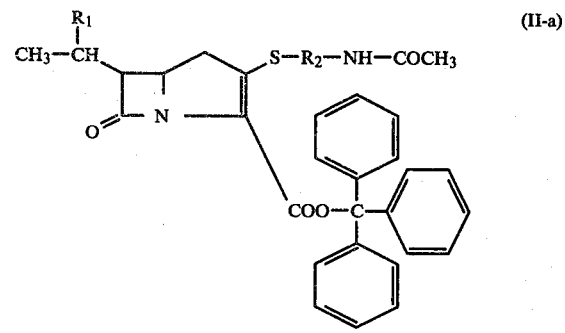

(II-a)

wherein $R_1$ and $R_2$ have the same meaning of above, is characteristic and useful in that it is more stable than antibiotic PS-6 or PS-7 of formula (I) so that it makes isolation easier and it has strong antibacterial and β-lactamase inhibitory activities, whereas the trityl ester of a known penicillin, for example, does not show any substantial antibacterial activity. It is presumably because the trityl group in the molecule of antibiotic PS-6 or PS-7 trityl ester of the invention is so active that it may be easily cleaved off in the assay medium or in vivo. The trityl ester of formula (II-a) is very important as an intermediate for synthesis of other pharmaceutically useful derivatives because the trityl group in the trityl ester of formula (II-a) is very active and can be easily cleaved off.

The physico-chemical and biological properties of the antibiotics PS-6 and PS-7 trityl ester of formula (II-a) which is provided by this invention are described in detail below.

(I) Antibiotic PS-6 trityl ester

Physico-chemical properties of the antibiotic PS-6 trityl ester (1) UV absorption spectrum
$\lambda_{max}^{CH_3OH} = 315.0$ nm
(2) Color reactions
Ehrlich reagent reaction: positive
Iodine-chloroplatinic acid reaction: positive
Ninhydrin reaction: negative
(3) Thin layer chromatography (TLC)
The following $R_f$ values are obtained on the following plates with the following solvents in TLC. ester.
DC-Fertigplatten Kieselgel 60 $F_{254}$ (E. Merck Co., Inc)
Benzene/Acetone (2/1): $R_f = 0.37$
Benzene/Ethylacetate (1/8): $R_f = 0.34$ Biological properties of the antibiotic PS-6 trityl ester (1) Antimicrobial spectra
The antibiotic PS-6 trityl ester of this invention has a broad antimicrobial spectrum, and shows very strong activity against various bacteria, for example, Gram-positive bacteria belonging to the genera Staphylococcus, Diplococcus, and Streptococcus and Gram-negative bacteria belonging to the genus Alcaligenes.

The antibiotic PS-6 trityl ester of this invention also shows good activity against Gram-negative bacteria belonging to the genus Klebsiella, Proteus and the like.

It is characteristic that the antibiotic PS-6 trityl ester shows strong activity against Gram-negative bacteria which are resistant to antibiotics having $\beta$-lactam ring in the structure, for example, those of the genera Citrobacter, Proteus, Klebsiella, and Serratia.

(2) Activity in vivo

The trityl ester of the antibiotic PS-6 showed a marked therapeutic effect when administered to mice infected with pathogenic Gram-positive bacteria.

(3) Toxicity

The trityl ester showed no acute toxicity when administered intraperitoneally to mice in a dose of 500 mg/kg.

(II) Antibiotic PS-7 trityl ester

Physico-chemical properties of the antibiotic PS-7 trityl ester (1) UV absorption spectrum
$\lambda_{max}^{CH3OH} = 321.0$ nm and
$\lambda_{max}^{CH3OH} = 230.5$ nm (2) Color reactions
Ehrlich reagent reaction: positive
Iodine-chloroplatinic acid reaction: positive
Ninhydrin reaction: negative (3) Thin layer chromatography (TLC)

The following $R_f$ values are obtained on the following plates with the following solvents in TLC.

DC-Fertigplatten Kieselgel 60 $F_{254}$ (E. Merck Co., Inc)

Benzene/Acetone (2/1): $R_f = 0.51$
Benzene/Ethylacetate (1/8): $R_f = 0.67$

Biological properties of the antibiotic PS-7 trityl ester (1) Antimicrobial spectra The antibiotic PS-7 trityl ester of this invention has a broad antimicrobial spectrum, and shows very strong activity against various bacteria, for example, Gram-positive bacteria belonging to the genera Staphylococcus, Diplococcus, and Streptococcus and Gram-negative bacteria belonging to the genus Alcaligenes.

The antibiotic PS-7 trityl ester of this invention also shows good activity against, for example, Gram-negative bacteria belonging to the genera Klebsiella, and Proteus.

It is characteristic that the antibiotic PS-7 trityl ester shows strong activity against Gram-negative bacteria which are resistant to the antibiotics having $\beta$-lactam ring in the structure, for example those of the Citrobacter, Proteus, Klebsiella, and Serratia.

(2) Activity in vivo

The trityl ester of antibiotic PS-7 showed a marked therapeutic effect when administered to mice infected with pathogenic Gram-positive bacteria.

(3) Toxicity

The trityl ester showed no acute toxicity when administered intraperitoneally to mice in a dose of 500 mg/kg.

The above-mentioned antibiotic PS-6 and PS-7 and the trityl ester thereof show sufficiently strong antimicrobial activities that they may be effectively employed for prevention and therapy of bacterial infections occurring not only in humans but also in animals, for example mammals, poultry and fish.

Furthermore, the trityl ester is very important as an intermediate for the synthesis of other useful pharmaceutics because the trityl group in the trityl ester of formula (II-a) is very active and is easily cleaved off.

The antibiotics PS-6 and PS-7 or the trityl ester thereof of this invention may be administered orally, topically or parenterally (intravenously, intramuscularly intraperitoneally, etc.) and may be used in any one of a variety of usual pharmaceutical depending on the route of administration. For example, the antibiotic PS-6 or the trityl ester thereof of this invention may be prepared with a pharmaceutically acceptable carrier or diluent in solid forms (for example, tablets, capsules, powders, granules, sugarcoated tablets, troches, powder sprays, suppositories, semi-solid forms (for example, ointments, creams, semi-solid capsules,), or liquid forms (for example, liquid solutions, emulsions, suspensions, lotions, syrups, solution for injection, liquid sprays,).

The unit dose preparation containing the antibiotic PS-6 or the trityl ester thereof of this invention may contain generally 0.1–99 weight %, preferably 10–60 weight % of the active component in any form of liquid, semi-solid and solid form.

Typical carriers, excipiens and diluents which can be used for these preparations and also methods of preparation are described below in more detail.

Tablets and capsules for oral administration may be in unit dose preparation form, and may contain binding agents, for example syrup, acacia, gelatin, sorbitol, tragacanth, or polyvinylpyrrolidone; excipiens, for example lactose, sucrose, starch, calcium phosphate, sorbitol, or glycine; lubricants, for example magnesium stearate, talc, polyethylene glycol, or silica; disintegrants, for example potato starch; or wetting agents such as sodium lauryl sulfate. The tablets may be coated according to methods well known in the art.

Liquid preparations for oral uses may be in the form of oily or aqueous suspensions, solutions, emulsions, syrups, etc., or may be provided as dry products to be mixed with water or other suitable carriers in use. The liquid preparations for oral uses may contain pharmaceutically acceptable additives, for example, suspending agents (for example, methyl cellulose, sorbitol syrup, sugar syrup, hydroxyethyl cellulose, gelatin, carboxymethyl cellulose, aluminum stearate gel, hydrogenated edible fats and oils); emulsifying agents (for example, acacia, lecithin, sorbitan monooleate); non-aqueous carriers (for example, ethyl alcohol, propylene glycol, oily esters, fractionated coconut oil, almond oil); and preservatives (for example, methyl p-hydroxybenzoate, propyl p-hydroxybenzoate, sorbic acid).

Suppositories may contain conventional suppository bases like cocoa butter and various glycerides.

Compositions for injection may be prepared in unit dose form in ampoules or in multidose containers with a preservative. They may be in the form of suspensions, solutions and emulsions in oily or aqueous vehicles, and if necessary, may contain formulatory agents such as suspending agents, dispersing agents and stabilizing agents. Alternatively, the antibiotic of the present invention may be prepared in the powder form reconstitutable in pyrogen-free, sterile water before use.

Compositions containing antibiotic PS-6 or PS-7 and/or the trityl ester of antibiotic PS-6 or PS-7 of the present invention may be provided in various forms suitable for absorption through the mucous membrane of the nose, throat and bronchial tube. For example, the form of powder or liquid sprays, inhalants, troches, throat paints, etc. will be advantageous for the above purposes. For treatment of the ears and eyes, the antibiotics of the present invention may be prepared as individual capsules, as drops, in liquid or semi-solid form, etc. In addition, for topical applications, it may be presented as formulations in hydrophilic or hydrophobic bases such as powders, lotions, creams, or ointments.

If desired, in addition to the carrier, the compositions described above may contain other ingredients, for example, preservatives, antioxidants, lubricants, viscosity agents, flavoring agents, suspending agents, binders, and stabilizing agents.

When antibiotic PS-6 or PS-7 and/or its trityl ester are intended for veterinary uses such as treatment of infections in pigs, cows, sheep, chickens and the like, the formulations may be presented as intramammary preparations in long-acting or quick-releasing bases, for instance, or as feed additive concentrates.

The above-described pharmaceutical compositions according to the present invention may contain antibiotic PS-6 or PS-7 and/or its trityl ester as the sole active ingredient or in combination with other therapeutically effective ingredients.

As described above in detail, because antibiotic PS-6 or PS-7 and its trityl ester of the present invention have a synergistic effect on various $\beta$-lactamase-producing bacteria in combination with $\beta$-lactam compounds, it will be advantageous to combine with $\beta$-lactam compounds in pharmaceutical compositions. As suitable examples of beta-lactam compounds, penicillin derivatives such as benzylpenicillin, phenoxymethyl-penicillin, carbenicillin, ampicillin and amoxicillin; and cephalosporin derivatives such as cephaloridine, cephalotin, cefazolin, cephalexin, cefoxitin, cephacetrile, cephamandole, cephapirin, cephradine and cephaloglycin can be listed.

When antibiotic PS-6 or PS-7 and/or its trityl ester is combined with one or more members of the above-listed beta-lactam compounds, the combining ratio of the antibiotic of this invention to the known beta-lactam compound should not be construed to be critical, but may vary in a wide range. But, from the practical viewpoint, it will be advisable to use the quantitative ratio of the antibiotic of this invention to the known beta-lactam compound(s) in the range of 20:1 to 1:150, and preferably 10:1 to 1:100.

In the treatment of bacterial infections in man, the dose of antibiotic PS-6 or PS-7 and/or its trityl ester can be varied depending on the object to be treated, the body weight, the type, severity and symptom of infections, the mode and number of administration, etc. For usual oral or paranteral administration, it will be profitable to use a daily dose in the range of 0.05 mg/kg to 500 mg/kg, preferably 0.5 mg/kg to 200 mg/kg preferably in a divided dosage. It will be well understood that a responsible physician can choose the dose beyond the above-recommended range, depending on the individual conditions of a patient to be treated.

Antibiotic PS-6 or PS-7 and/or its trityl ester can be used as pharmaceutical compositions described above or may be added directly or as feed additive concentrates in animal feeds. In addition, they may be utilized as active ingredients for food preservatives or disinfectants.

DESCRIPTION OF SOME PREFERRED EMBODIMENTS

The following examples illustrate the present invention. In all examples, the quantitative and qualitative assays of antimicrobial activity were based on the following methods:

(1) Bio-assay of antimicrobial activity

The overnight culture of *Comamonas terrigena* B-996 on a nutrient agar slant was suspended in nutrient broth so as to give a seed culture of an optical cell density of 0.040 at 610 nm. The seed suspension was added in a 1% amount to molten agar medium containing 0.8% Kyokuto Nutrient Broth Powder (Kyokuto Pharmaceutical Industries Co.) and 1.0% Bacto-Agar (Difco Laboratories). Each 7 ml of the seeded molten agar medium was distributed in a Petri dish (9 cm in diameter) and solidified. This is called a Comamonas assay plate.

*Staphylococcus aureus* FDA 209P was cultivated overnight in nutrient broth with shaking and diluted 50 fold in nutrient broth to provide the seed suspension. The molten agar medium containing 1% Kyokuto Nutrient Broth Powder (Kyokuto Pharmaceutical Industries Co.) and 1% Bacto-Agar (Difco Laboratories) were inoculated well with a 1% (v/v) amount of the seed suspension. Seven milliliters each of the above seeded molten agar medium was poured and gelled in a Petri dish (9 cm in diameter). This is called as a Staphylococcus assay plate.

Similarly, an Alcaligenes assay plate was prepared. That is, the one night-old nutrient agar slant culture of *Alcaligenes faecalis* B-326 was suspended in nutrient broth to provide the seed suspension, the cell concentration of which was adjusted to an optical of 0.020 at 610 nm. Agar medium composed of 0.5% Kyokuto Nutrient Broth Powder (Kyokuto Pharmaceutical Industries Co.) and 1.0% Bacto-Agar (Difco Laboratories) was melted at a permissible temperature and inoculated with a 1.0% inoculum of the seed suspension which was distributed in an amount of 7.0 ml into a 9 cm Petri dish and allowed to gel. This is termed an Alcaligenes assay plate.

A pulp disc of 8 mm diameter was usually soaked with a sample solution to be assayed; left then on a clean sheet of filter paper for a sufficient time to remove an excess solution; transferred onto an assay plate; and incubated at 35° C. for 20 hours. The diameter of the observed inhibition zone was measured and compared with standard solutions of cephaloridine. The antimicrobial activity of antibiotic PS-6 and related compounds is expressed as cephaloridine equivalent units/ml.

More particularly, a solution of antibiotic PS-6 and related compounds of the present invention which shows the same diameter of inhibition zone as 100 μg/ml of cephaloridine is expressed as 100 cephaloridine units/ml. Similarly, when a solid sample of antibiotic PS-6 and related compounds of this invention exhibits at a concentration of 1 mg/ml the same diameter as 1 μg/ml of cephaloridine; the specific activity of the solid sample is shown as 1 cephaloridine unit/mg. As is well known to those skilled in the art, the assay standard curve varies to some extent, depending on the species of the test microorganisms. To specify the species of the test microbes, the following unit expressions were employed Comamonas-cephaloridine unit (abbreviated as CCU); Staphylococcus-cephaloridine unit (abbreviated as SCU); and Alcaligenes-cephaloridine unit (abbreviated as ACU).

(2) Bio-autography

A large assay plate was prepared as described in (1). Bioassay of antimicrobial activity, except that 100 ml of the seeded molten agar medium was poured in a rectangular dish of 32×24 cm instead of a 9 cm Petri dish.

A paper chromatogram to be assayed was placed for 15 minutes on the said large assay plate. After the paper was removed, the assay plate was incubated at 35° C. for 20 hours to reveal the inhibition zone. This permitted the inventors not only to calculate the $R_f$ value(s) (qualitative assay) but also to determine the antimicrobial activity (semi-quantitative assay) based on the size of the inhibitory zone.

In the case of the TLC plate, a sheet of thin paper was intercalated between the TLC plate and the surface of the assay plate. The similar procedure was carried out for qualitative and semi-quantitative assays.

EXAMPLE 1

A 500 ml Erlenmeyer flask containing the following seed culture medium (SE-4) was sterilized at 120° C. for 15 minutes. To a well-sporulated slant culture of Streptomyces sp. A271, 10 ml of 0.02% Tween-80 (a surfactant, Trademark of Atlas Powder Corp.) solution was poured and stirred lightly to produce a spore suspension. One milliliter of the spore suspension was inoculated in to the 500 ml Erlenmeyer flask and shake-cultured at 28° C. for 48 hours on a rotary shaker (200 r.p.m.; radius of circle 3.5 cm). Then 2 ml of the seed culture was inoculated into a 500 ml Erlenmeyer flask containing 100 ml of the following production media and shake-culture at 28° C. for 48 to 96 hours on a rotary shaking machine:

| SEED CULTURE MEDIUM (SE-4) | |
|---|---|
| Beef extract (Difco Laboratories) | 0.3% (w/v) |
| Bacto-tryptone (Difco Laboratories) | 0.5% (w/v) |
| Glucose | 0.1 |
| Soluble starch | 2.4 |
| Yeast extract | 0.5 |
| Calcium carbonate | 0.4 |
| Defatted soybean meal | 0.5 |
| pH 7.5 prior to sterilization | |

| PRODUCTION MEDIUM | |
|---|---|
| (1) AG-1 medium | |
| Glucose | 1.5% (w/v) |
| Corn starch | 2.5 |
| Corn steep liquor | 2.0 |
| Dry yeast | 1.0 |
| D,L-methionine | 0.1 |
| $CoCl_2.6H_2O$ | 0.00013 |
| pH 7.2 prior to sterilization | |
| (2) AGA-2 medium | |
| Glucose | 1.5% (w/v) |
| Potato starch | 2.5 |
| Corn steep liquor | 2.0 |
| Dry yeast | 1.0 |
| $CoCl_2.6H_2O$ | 0.00013 |
| pH 6.5 prior to sterilization | |
| (3) AGB-medium | |
| Maltose | 3.0% (w/v) |
| Corn steep liquor | 1.0 |
| Dry yeast | 1.0 |
| $CoCl_2.6H_2O$ | 0.0001 |
| pH 6.5 prior to sterilization | |

| PRODUCTION MEDIUM -continued | |
|---|---|
| (4) AGB-41 medium | |
| Maltose | 5.0% (w/v) |
| Soluble starch | 1.0 |
| Glycerin | 0.3 |
| Dry yeast | 2.5 |
| NaCl | 0.5 |
| $K_2HPO_4$ | 0.05 |
| $MgSO_4.7H_2O$ | 0.05 |
| $CaCO_3$ | 0.3 |
| $CoCl_2.6H_2O$ | 0.00013 |
| pH 7.0 prior to sterilization | |
| (5) ML-19 medium | |
| Glycerin | 4.0% (w/v) |
| Peptone | 0.5 |
| Glucose | 0.2 |
| Potato starch | 0.2 |
| Defatted soybean meal | 0.5 |
| Dry yeast | 0.5 |
| NaCl | 0.5 |
| $CaCO_3$ | 0.2 |
| pH 6.4 prior to sterilization | |
| (6) AGO-1 medium | |
| Soybean oil | 3.0% (w/v) |
| Dry yeast | 2.0 |
| NaCl | 0.5 |
| $K_2HPO_4$ | 0.05 |
| $MgSO_4.7H_2O$ | 0.05% (w/v) |
| $CaCO_3$ | 0.3 |
| $CoCl_2.6H_2O$ | 0.00013 |
| pH 7.0 prior to sterilization | |

A small quantity of cultured broth was sampled from each flask at regular intervals. The active components in the samples were extracted and concentrated and the presence of antibiotics PS-6 and PS-7 were detected by paper chromatography and bioautography as described below.

Detection of antibiotic PS-6

10 ml of supernatant liquid of centrifuged cultured broth is eluted in a mini-column including 1.5 ml of Diaion HP-20 (ion exchanger, Mitsubishi Chemical Industries Ltd.). After the active component is absorbed, it is eluted with acetone aqueous solution (50% v/v). 0.5 ml of eluate at the beginning is discarded and 2 ml of subsequent eluate is taken. The eluate is concentrated, and 20 $\mu$l of the concentrated eluate is subjected to descending paper chromatography with filter paper (Toyo Roshi No. 50, Toyo Roshi Kaisha) by developing at 5° C. for 7-20 hours with various kinds of solvents. After the development, the filter paper while still moist is attached to an assay plate for bioautography using various kinds of microorganisms for 15-30 min. The filter paper is then removed and the assay plate is then cultivated at 30° C. for about 18 hours. A sample including antibiotic PS-6 forms an inhibition zone at $R_f$ position of antibiotic PS-6. According to the method described above, the antibiotic PS-6 was detected in the cultured broths of 6 media described above.

Detection of the antibiotic PS-7

A 10 ml-portion of supernatant obtained by centrifugation of the cultured broth was applied to a mini-column packed with 1.5 ml of Diaion PA-306 (Mitsubishi Chemical Industries Ltd.). The column was washed with 0.5 ml of 5% (W/V) sodium chloride solution and eluted with 50% (W/V) methanol solution containing 3% (W/V) sodium chloride. The first 1.0 ml of the eluate was discarded and 5.0 ml of the succeeding eluate was collected. The eluate was, after evaporated under reduced pressure to remove methanol, applied to a mini-column packed with 1.5 ml Diaion HP-20 (Mitsubishi Chemical Industries Ltd.). An active component adsorbed on the resin was eluted with 50% (V/V) acetone solution. The first 0.5 ml of the eluate was discarded and 2.0 ml of the succeeding eluate was collected. The eluate was concentrated and 20 μl of the resulted concentrate was spotted on Toyo filter paper No. 50 (Toyo Roshi Co.). Descending paper chromatography was accomplished with various solvent systems at 5° C. for 7-20 hours. After development, the half-dried chromatograms were contacted for 15-30 minutes with the agar surface of assay plates for bioautography containing various test microorganisms, respectively. The assay plates were incubated at 35° C. for 18 hours. A sample containing the antibiotic PS-7 gives a growth inhibitory zone at the position of $R_f$ value of the antibiotic PS 7.

Results obtained according to the procedure mentioned above showed that the antibiotic PS-7 was detected in all broth filtrates obtained by using the above-mentioned four kinds of medium, although their amounts of accumulation were different from one another.

EXAMPLE 2

Streptomyces sp. A271 was cultivated in a similar way of Example 1 except using the undermentioned medium AGB-42. Before, or 24 hours after, the commencement of cultivation, 0.2% of DL-valine of L-valine was added to the medium. The amount of the antibiotic PS-6 accumulated in the cultured broth after shaking the culture for 72 hours was more than four times that in the cultured broth of control in which valine was not added.

| Composition of medium (AGB-42) | |
|---|---|
| Maltose | 5.0% (w/v) |
| Soluble starch | 1.0% (w/v) |
| Glycerine | 0.3% (w/v) |
| Dry yeast | 3.0% (w/v) |
| NaCl | 0.5% (w/v) |
| $K_2HPO_4$ | 0.05% (w/v) |
| $MgSO_4.7H_2O$ | 0.05% (w/v) |
| $CaCO_3$ | 0.3% (w/v) |
| $CoCl_2.6H_2O$ | 0.00013% |
| pH 7.0 Prior to sterilization | |

EXAMPLE 3

Streptomyces sp. A271 was cultivated in a similar way to Example 1 except using the ML-19 medium described above. Before, or 24 hours after, the commencement of cultivation, 0.2% of DL-valine or L-valine was added to the medium. After shaking the culture for 72 hours, the amount of antibiotic PS-6 accumulated in the broth was more than four times that in the cultured broth of the control in which valine was excluded.

EXAMPLE 4

Streptomyces sp. A271 was cultivated in a similar way to Example 3 except adding DL- or L-leucine instead of DL- or L-valine. After shaking the culture for 72 hours, the amount of the antibiotic PS-6 accumulated was more than two times that in the cultured broth of the control in which leucine was excluded.

EXAMPLE 5

Streptomyces sp. A271 was cultivated in a similar way to Example 1 except using the undermentioned medium AGB-3. Before the cultivation, 0.1% of L-valine and 0.3% of L-leucine was added into the medium. After shaking the culture for 72 hours, a substantial amount of antibiotic PS-6 was accumulated in the broth.

| Composition of medium (AGB-3) | |
|---|---|
| Maltose | 3.0% (w/v) |
| Dry yeast | 2.0% |
| NaCl | 0.5% |
| $K_2HPO_4$ | 0.05% |
| $MgSO_4.7H_2O$ | 0.05% |
| $CaCO_3$ | 0.3% |
| $CoCl_2.6H_2O$ | 0.00013% |
| pH 7.0 prior to sterilization | |

EXAMPLE 6

A similar cultivation as described in Example 2 was conducted in which n-valerianic acid was added instead of DL- or L-valine. The amount of the antibiotic PS-6 accumulated in the broth after shaking the culture for 72 hours was more than four times that in the broth of control in which n-valerianic acid was excluded.

EXAMPLE 7

A similar cultivation as described in Example 3 was conducted in which n-valerianic acid was added instead of DL- or L-valine. The amount of the antibiotic PS-6 accumulated was more than two times that in the broth of control in which n-valerianic acid was not added.

EXAMPLE 8

A similar cultivation as described in Example 5 was conducted in which n-valerianic acid was added instead of L-valine. The amount of the antibiotic PS-6 accumulated in the cultured broth was more than four times that in the broth of the control in which n-valeric acid was excluded.

EXAMPLE 9

One hundred milliliters of the seed culture prepared as described in Example 1 was transferred into a 30 liter jar fermentor containing 15 liters of SE-4 medium, mentioned above, and cultivated under forced aeration at 28° C. for 24 hours at 200 r.p.m., the sterile air being fed at 7.5 liter/minute. 1 liter of the medium was inoculated into 100 l of the above mentioned AGB-42 medium (0.5% of L-valine was added prior to the inoculation) in a 200 l-volume stainless fermentor, and cultivated under forced aeration at 50 l/minute at 28° C. for 72 hours at 100 r.p.m. The antibiotic potency of the broth centrifuged supernatant was 450 CCU/ml. To the broth, 3% (w/v) of perlite filter aid (Topco Perlite, Topco No. 34, Toko Perlite Kogyo K.K.) was added, and it was filtered through a filter-press to produce 60 l of filtrate (the total antibiotic activity: $25.5 \times 10^6$ CCU).

All the following operations were conducted under cooled conditions below 6° C. The filtrate was adsorbed on a column packed with 6 l of ion-exchange resin, Diaion PA-306 (Mitsubishi Chemical Industries Ltd.). The column was eluted with 20 l of 5% (W/V) sodium chloride solution to obtain the active fraction (A) containing antibiotics PS-5 and PS-6 (the total antibiotic activity: $4.2 \times 10^6$ CCU). The column after this elution will be employed later for isolation of antibiotics PS-7. The active fraction (A) was charged through a Diaion HP-20 resin (Mitsubishi Chemical Industries Ltd.) ($3 \times 70$ cm) column followed by elution with 10% aqueous acetone solution. The eluate was concentrated under reduced pressure to distill off acetone, and passed through a column ($2.4 \times 22$ cm) of QAE-Sephadex (Pharmacia Fine Chemicals Co.) previously equilibrated to pH 8.0 with 1/100 phosphate buffer solution, and elution was carried out with a linear sodium chloride gradient concentration of M/100 phosphate buffer solution from 1 to 0.4 M of NaCl concentration, and collected eluates in 10 g fractions. The collected fractions were diluted to 100 times and the active fractions were collected after detecting by UV absorption spectrum and bioassay. To remove completely the antibiotic PS-5 contained, the active fraction was charged through a column ($1.2 \times 40$ cm) of Dianion HP-20 AG (Mitsubishi Chemical Industries Ltd.) and eluted with 300 ml of linear methanol gradient concentration of methanol aqueous solution from 10 to 75%. The volume of each fraction was 4 g. Each fraction was subjected to descending paper chromatography (developed with a mixed solvent composed of 120 ml of acetonitril, 30 ml of 1/10 M Tris (hydroxymethyl) aminomethane-HCl buffer solution (pH 7.5) and 1 ml of 1/10 M sodium ethylenediamine tetra acetate aqueous solution (pH 7.5) and analyzed by bio-autography. Active fractions from No. 25 to 30 containing the antibiotic PS-5 and active fractions from No. 33 to 40 containing the antibiotic PS-6 were collected. The active fraction containing antibiotic PS-6 was concentrated and, after methanol was distilled off, it was freeze-dried. The lyophilized preparation thus obtained was dissolved in 1 ml of M/100 phosphate buffer solution (pH 8.0) and then charged for purification through a column ($1.2 \times 80$ cm) of Sephadex G-10 (Pharmacia Fine Chemicals Co.) and developed with the same buffer solution. The active fractions were collected and adjusted with dilute NaOH aqueous solution to pH 8.3, and then charged through a column ($1.2 \times 20$ cm) of Diaion HP-20 resin (Mitsubishi Chemicals Industries Ltd.). The elution was carried out with 10% aqueous acetone solution for desalting. The active fraction was collected and freeze-dried to produce 2.4 mg of white lyophilized preparation of the antibiotic PS-6 sodium salt. The column of Diaion PA-306 (Mitsubishi Chemical Industries Ltd.) which was eluted with sodium chloride solution and had been kept for isolation of antibiotic PS-7 was eluted with 50% (V/V) aqueous methanol containing 3% (W/V) sodium chloride to obtain the active fraction (B) (Total antimicrobial activity: $1.1 \times 10^6$ CCU, 4.3% yield).

The eluate of the active fraction (B), after concentrated under reduced pressure to remove methanol, was adsorbed on a column (3 cm$\phi \times 70$ cm) packed with Diaion HP-20 (Mitsubishi Chemical Industries Ltd.) and eluted with 10% (V/V) aqueous acetone. The eluate was factionated in each 25 g portion.

Active fractions were combined and concentrated under reduced pressure to remove acetone. The concentrate was adsorbed on a QAE-Sephadex (Pharmacia Fine Chemicals AB) column (2.5 cm$\phi \times 30$ cm) previously bufferized with M/1000 phosphate buffer solution, pH 8.0 and eluted with a linear gradient of sodium chloride concentration from 0.1 to 0.7 M in M/100 phosphate buffer. The eluate was fractionated in each 17 g portion. Each fraction was analyzed by bioassay and paper chromatography followed by bioautography, and fractions from No. 25 to No. 33 was collected and combined, in which the antibiotic PS-7 was contained.

The above active fraction was adsorbed on a column (1.1 cm$\phi \times 20$ cm) packed with Daiaion HP-20AG (Mitsubishi Chemical Industries Ltd.) and eluted with a linear gradient of acetone concentration from 0 to 10% in a total volume of 400 ml. The eluate was fractionated in each 5 g-portion. Each fraction was diluted 50 times for ultraviolet spectroscopic analysis. Fractions from No. 15 to No. 20 in which the antibiotic PS-7 was contained were collected and lyophilized to yield crude preparation of the antibiotic PS-7.

For the further purification of the antibiotic PS-7, the lyophilized crude preparation of the antibiotic PS-7 thus obtained was dissolved in M/100 phosphate buffer solution, pH 8.0 and charged on a Sephadex G-10 (Pharmacia Fine Chemicals AB) column (1.2 cm$\phi \times 80$ cm), and then developed with the same phosphate buffer solution. Active fractions were combined and adsorbed on a QAE-Sephadex (Pharmacia Fine Chemicals AB) column (1.1 cm$\phi \times 20$ cm) previously bufferized with M/100 phosphate buffer solution, pH 8.0 and eluted with a linear gradient of sodium chloride concentration from 0 to 0.4 M in a total volume of 200 ml. Active fractions from the column were combined. To the fraction was added sodium chloride at a concentration of 3% (W/V). The solution was adsorbed on a Diaion HP-20AG (Mitsubishi Chemical Industries Ltd.) column (1.1 cm$\phi \times 20$ cm) and an active component was eluted with 10% (V/V) aqueous acetone and desalted. The active fraction was lyophilized to yield 1.5 mg of sodium salt of the antibiotic PS-7 in white lyophilized preparation.

Similar procedures were repeated to obtain the preparations.

Sodium salts of the antibiotics PS-6 and PS-7 thus obtained showed the following physicochemical properties, respectively.

I. Antibiotics PS-6

(1) Color

Colorless (2) Solubility

Soluble in water and substantially insoluble in acetone (3) Decomposition point

When measured in a Kofler micromelting point apparatus BY-1 (YAZAWA Scientific Mfg. Co., Ltd.) with the temperature raised at a rate of 1° C./minute, this preparation did not show a clear melting point. It began to soften around 143° C. and gradually turned brown and began to shrink in volume at 165° C. Around 220° C., the tint of the preparation slowly changed to brown resin.

(4) Ultraviolet absorption spectrum

Sixty micrograms of antibiotic PS-6 sodium salt was dissolved in 3.0 ml of water and measured in a Hitachi Double-beam Spectrophotometer Model 200-20 (Hitachi, Ltd.). The recorded chart is shown in FIG. 1. The following are the characteristic values:

$\lambda_{min.}{}^{H_2O}$ = approximately 243.0 nm $\lambda_{max.}{}^{H_2O}$ = approximately 300.0 nm To an aqueous solution of this preparation in distilled water, a hydroxylamine solution (pH 7.5) was added to bring the concentration of PS-6 to 20 μg/ml and that of the later to 10 mM. After 30 minutes at 22° C., the reaction mixture lost ca. 95% of the initial optical density at 300.0 nm.

(5) Infrared absorption spectrum

Figure 2:
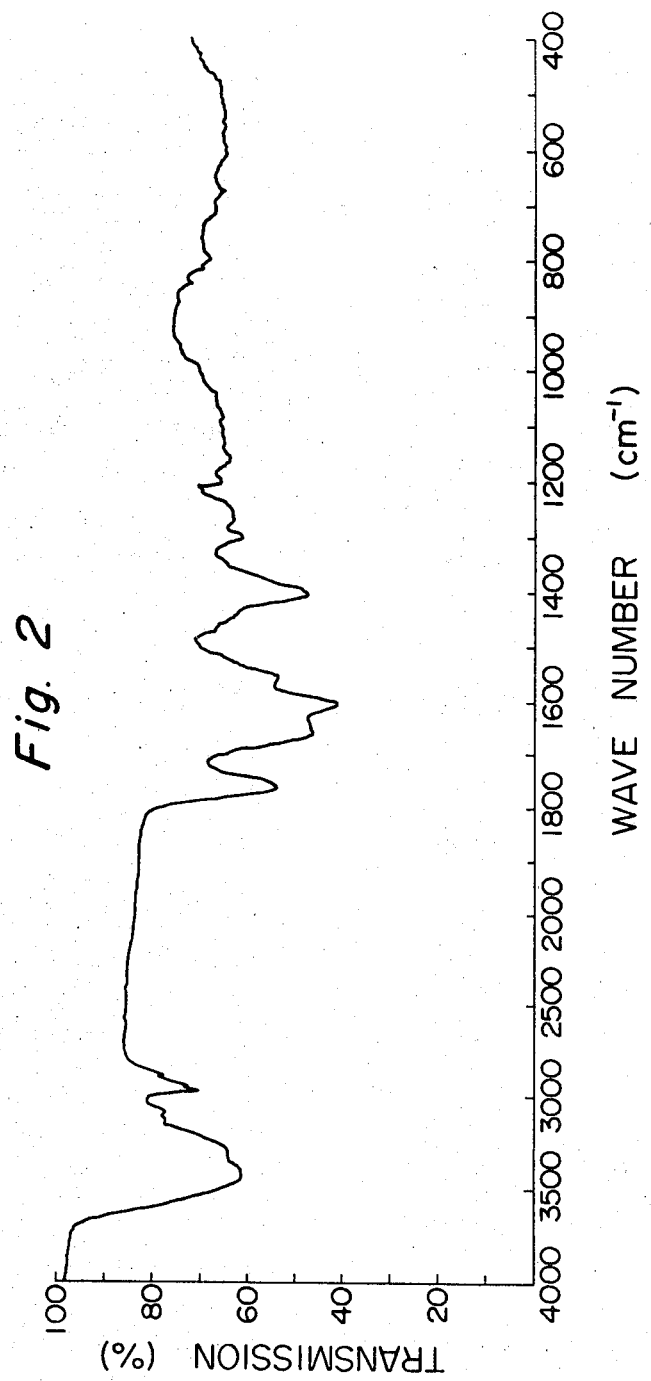
FIG. 2 shows the infrared absorption spectrum of antibiotic PS-6 sodium salt in KBr.

FIG. 2 shows the infrared absorption spectrum of antibiotic PS-6 sodium salt in KBr recorded on a Hitachi Infrared Spectrophotometer Model 215 (Hitachi, Ltd.). The following characteristic absorption maxima were located at the indicated wave numbers:
(i) ca. 1760 $cm^{-1}$ (—CO— in the beta-lactam ring)
(ii) ca. 1660 $cm^{-1}$ (—CO— in the amide bondage)
(iii) ca. 1600 $cm^{-1}$ (—COO$^\ominus$)
(iv) ca. 1555 $cm^{-1}$ (—CO—NH— in the amide bondage)

(6) Proton nuclear magnetic resonance spectrum

Figure 3:
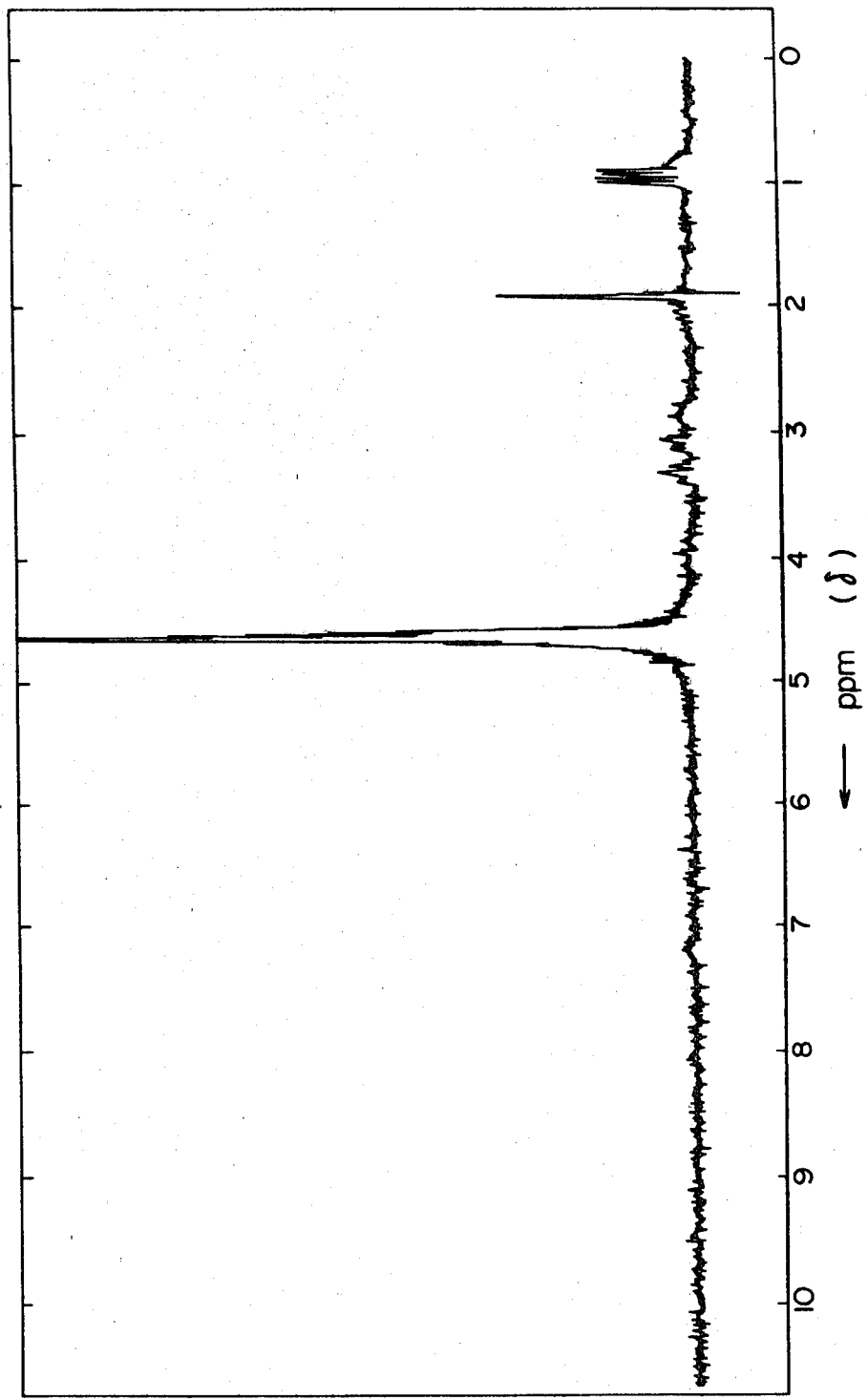
FIG. 3 is the 100 MHz proton nuclean magnetic resonance spectrum of antibiotic PS-6 sodium salt in heavy water.

The attached chart FIG. 3 is the 100 MHz proton nuclear magnetic resonance spectrum of antibiotic PS-6 sodium salt in heavy water recorded in a JEOL NMR spectrometer JNM PS-100 (Japan Electron Optics Laboratory Co., Ltd.). The following characteristic signals were confirmed:
(i) a pair of doublets that has the center around 0.94 ppm and around 0.98 ppm (J=ca. 7.0 Hz)

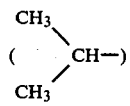

(ii) a sharp singlet around 1.92 ppm ($CH_3$—CO—)
(iii) a multiplet in the region of around 2.42–3.50 ppm

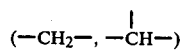

(iv) a multiplet in the region of around 3.90–4.20 ppm

(7) Color reaction
Ehrlich reagent reaction: positive
Iodine-chloroplatinic acid reaction: positive
Ninhydrin reaction: negative (8) Paper chromatography The antibiotic PS-6 showed the following $R_f$ values with Toyo Filter Paper No. 50 (Toyo Roshi Kaisha Ltd.) and with the following solvents by descending paper chromatography:
Acetonitrile/Tris buffer/EDTA (Note 1): $R_f$=0.41
Ethanol/water (7/3): $R_f$=0.65
(Note 1: A solvent mixture composed of 120 ml of acetonitrile, 30 ml of 1/10 M Tris (hydroxylmethyl) aminomethane-HCl buffer solution (pH 7.5) and 1 ml of 1/10 M sodium ethylenediaminetetraacetate aqueous solution (pH 7.5).)

(9) Thin layer chromatography (TLC)

The antibiotic PS-6 was subjected to chromatogram sheet 13254 cellulose (Eastman Kodak Co.) with the following solvents and showed the following $R_f$ values.
n-butanol/ethanol/water (4/1/5) the upper layer: $R_f$=0.67
n-propane/water (8/2): $R_f$=0.69
n-butanol/i-propanol/water (7/7/6): $R_f$=0.70
acetonitrile/water (8/2): $R_f$=0.68

(10) High voltage paper electrophoresis

The antibiotic PS-6 was analyzed by high voltage paper electrophoresis under the indicated conditions. The apparatus was a product of Savant Instruments Inc. (High Voltage Power Supply, Model No. HV 3000A and Flat Plate Electrophoresis, Model No. FP 18A). The filter paper employed for this analysis was Toyo Filter Paper No. 50. The results are as follows:

When electrophoresis was carried out for 30 minutes under cooling (below 4° C.) at a potential of 42 V/cm in a buffer solution (pH 8.6) containing 3.3 g of Barbital and 25.5 g of sodium Barbital in 3000 ml of water, antibiotic PS-6 moved 28 mm towards the anode.

The physico-chemical properties described above show that the molecular structure of the antibiotic PS-6 preparation in this example can be expressed as follows:

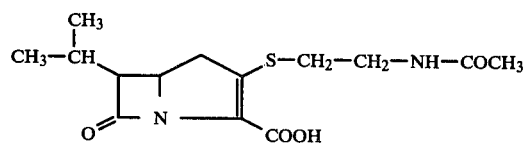

The following biological properties were confirmed with the antibiotic PS-6 sodium salt preparation in this example:

(1) Antimicrobial spectrum

The MIC values of antibiotic PS-6 sodium salt were determined on various pathogenic microorganisms including resistant strains by the broth dilution method utilizing BRAIN HEART INFUSION BROTH 'Eiken' (EIKEN CHEMICAL CO., LTD.).

The antibiotic PS-6 sodium salt preparation was dissolved in BRAIN HEART INFUSION BROTH 'Eiken' (EIKEN CHEMICAL CO., LTD.) (pH 7.0) at concentrations in the range of 5–100 μg/ml, from which appropriate dilution series were made in the same liquid medium. The microorganisms listed in Table 5 were cultivated for 18 hours in BRAIN HEART INFUSION BROTH 'Eiken' at 28° C. and inoculated into the dilution series of antibiotic PS-6 at a final inoculum size of $1 \times 10^5$ cells/ml. After standing culture at 35° C. for 20 hours, the growth of the microorganisms was read in each dilution of antibiotic PS-6. The minimum inhibitory concentration (MIC) represents the smallest concentration of the antibiotic PS-6 sodium salt preparation where no propagation of the relevant microorganism was visually confirmed. As the controls, two known beta-lactam antibiotics, cefazorin and cefoxitin were dissolved in BRAIN HEART INFUSION BROTH at pH 7.0 at concentrations ranging from 1 μg/ml to 100 μg/ml; diluted to make several dilution series in the said liquid medium; and treated as described above for the MIC determinations. Table 5 summarizes the obtained results. In addition to the MIC values of antibiotic PS-6, those of cefazorin and cefoxitin are included for reference.

TABLE 5

| Microorganism | Minimum inhibitory concentration (μg/ml) | | |
|---|---|---|---|
| | Antibiotics PS-6 | Cefazorin | Cefoxitin |
| *Staphylococcus aureus* FDA.209P | 0.33 | 0.25 | 2.50 |
| *Staphylococcus aureus* Bx-1633 | 0.33 | 0.50 | 2.50 |

TABLE 5-continued

| Microorganism | Minimum inhibitory concentration (μg/ml) | | |
|---|---|---|---|
| | Antibiotics PS-6 | Cefazorin | Cefoxitin |
| Staphylococcus aureus Rassell | 1.34 | 1.0 | 5.0 |
| Diplococcus pneumoniae Type III[4*] | 0.17 | 0.125 | 2.50 |
| Streptococcus pyogenes NY-5[4*] | 0.33 | 0.25 | 1.25 |
| Bacillus subtilis ATCC 6633 | 1.34 | 0.50 | 1.25 |
| Alcaligenes faecalis B-326 | 1.56 | 6.25 | 1.56 |
| Citrobacter freundii E-9* | 12.5 | >100 | >100 |
| Serratia marcescens S-18* | 50.0 | >100 | 50.0 |
| Klebsiella pneumoniae K-2* | 12.5 | 6.25 | 6.25 |
| Enterobacter sp. E-8* | 12.5 | 3.13 | 12.5 |
| Enterobacter cloacae E-16* | 25.0 | >100 | >100 |
| Enterobacter aerogenes E-19* | 25.0 | >100 | >100 |
| Proteus vulgaris P-5 | 25.0 | >100 | |
| Proteus rettgeri P-7[3*] | 6.25 | 25.0 | |
| Proteus mirabilis P-6[2*] | 12.5 | 6.25 | |
| Proteus sp. P-22 | 12.5 | >100 | |
| Providencia sp. P-8[2*] | 12.5 | 50.0 | |

Note:
*beta-lactamase producer
[2*]resistant to kanamycin, gentamycin and tobramycin
[3*]resistant to gentamycin and tobramycin
[4*]10% horse blood supplemented into the medium (2) Potentiating and synergistic effect of the antimicrobial activity of known beta-lactam compounds against β-lactam-resistant microorganisms 10 ml of 2.5 folds diluted nutrient agar (pH 7.0) containing 50 μg/ml of penicillin G or cephaloridine was seeded with the β-lactamase producing and β-lactam-resistant microorganisms and poured in a 9 cm Petri dish to provide the bio-assay agar plate. On this assay plate, 8 mm of pulp discs each containing 20 μl of antibiotic PS-6 solution at the concentration of 240 μg/ml were placed and incubated at 35° C. for 18 hours before reading the inhibition zones. A control assay plate was similarly prepared without penicillin G or cephaloridine. As reference antibiotics, 10,000 μg/ml of penicillin G or 20 μl of cephaloridine were disc-assayed under the same conditions. The results are shown in Table 6.

From the results shown in Table 6, the addition of antibiotic PS-6 to penicillin G or cephaloridine at a concentration below the detectable limit showed clearly the synergistic effect against β-lactam-resistant microorganisms. The addition of penicillin G or cephaloridine instead of the antibiotic showed no synergistic effect.

TABLE 6

| β-lactam resistant microorganism | Disc | Inhibition zone (mm) | | |
|---|---|---|---|---|
| | | Control | with penicillin G | with cephaloridine |
| Proteus vulgaris P-5 | PS-6 | 14.0 | 30.0 | 28.5 |
| | penicillin G | 15.0 | 15.0 | 15.0 |
| | cephaloridine | 12.0 | 12.0 | 12.0 |
| Citrobacter freundii E-9 | PS-6 | 22.0 | 23.0 | 25.0 |
| | penicillin G | 0.0 | 0.0 | 0.0 |
| | cephaloridine | 12.0 | 12.0 | 12.0 |
| Serratia marcescens S-18 | PS-6 | 20.0 | 22.0 | 26.0 |
| | penicillin G | 0.0 | 0.0 | 0.0 |
| | cephaloridine | 11.0 | 11.0 | 11.0 |

(3) In vivo activity

The therapeutic activity of the antibiotic PS-6 sodium salt preparation was studied by treating mice that were intraperitoneally infected with $5 \times 10^5$ cells/mouse of Staphylococcus aureus Smith. Soon after infection, an aqueous solution of the antibiotic PS-5 sodium salt preparation was subcutaneously injected. In DDY male mice (Shizuoka), the 50% curative dose of this preparation was found to be 5.2 mg/kg.

(4) Toxicity

Aqueous solution for injection of the antibiotic PS-6 sodium salt preparation was intraperitoneally administered to DDY male mice (Shizuoka) at the dose of 500 mg/kg. No acute toxicity was recorded.

(5) Susceptibility to known beta-lactamases (Properties of antibiotic PS-6 as the enzymic substrate)

Susceptibility to beta-lactamase of the antibiotic PS-6 sodium salt preparation as the enzymic substrate was studied against exo-penicillinase of Bacillus licheniformis 749/C (ATCC 25972) and inducible penicillinase of Bacillus cereus 569 (ATCC 27348) under the following reaction conditions:

(A) Reagent (1) Substrate
The antibiotic PS-6 sodium salt preparation was dissolved in 25 nM phosphate buffer (pH 6.8) at the indicated concentrations.

(2) Beta-lactamase
(a) Exo-penicillinase of Bacillus licheniformis 749/C (ATCC 25972). Purified by cephalexin-Sepharose 4B (Pharmacia Fine Chemicals AB) affinity column chromatography. The potency of this enzyme preparation was 16,600 units/ml. when the hydrolysis of potassium penicillin G was measured by iodometry at 30° C. in M/10, pH 6.8, phosphate buffer. One unit of penicillinase means the amount of enzyme that can hydrolyze 1 micromole of penicillin G for 60 minutes at 30° C. with a pH 6.8.

(b) Inducible penicillinase of Bacillus cereus 569 (ATCC 27348). This beta-lactamase was induced by ampicillin and purified by CM-cellulose column chromatography. This preparation had a titer of 26,900 potassium penicillin G units/ml.

(B) Reaction and assay conditions

To a 1 cm quartz cuvette containing 3 ml of the buffered solution of the antibiotic PS-6 sodium salt preparation at 30° C., beta-lactamase was added in the indicated amounts and instantly mixed well to start the reaction. Time course of the hydrolysis was traced at 30° C. by determining the decrease in optical density at 301 nm which corresponds specifically to the concentration of antibiotic PS-6. As described in Japanese Patent Application No. 94651/77, the antibiotic PS-5 sodium salt preparation gave a $E_{1\,cm}^{1\%}$ value of 267.5 at the λmax of 301 nm. If this preparation contained no water of crystallization, its epsilon value would be 8560.

As 5% of the initial optical density of antibiotic PS-5 at 301 nm remained even after the complete decomposition with hydroxylamine or beta-lactamase, the differential optical density of this substrate at 301 nm was supposed to be $\Delta\epsilon = 8132$. This was supposed to be applicable to the antibiotic PS-6, and the following calculation was carried out.

(C) Results (a) Exo-penicillinase of Bacillus licheniformis 749/C. A half milliliter of the above enzyme preparation and 2.5 ml of the substrate solution containing 30 mμ moles of antibiotic PS-6 was mixed (final concentration of antibiotic PS-6 = 10 pmoles/ml = 3.3 μg/ml; Initial optical density at 301 nm = 0.086) and incubated for 15 minutes under the above specified conditions, without a substantial hydrolysis of antibiotic PS-6.

(b) Inducible penicillinase of *Bacillus cereus* 569. Time course of the hydrolysis of antibiotic PS-6 by this beta-lactamase was followed under the above-described conditions by determining the optical density at 301 nm of the reaction mixtures containing 7.5 μl of the above mentioned enzyme preparation and 77.5 pmoles of antibiotic PS-6 as the substrate in a total of 3.0 ml (final concentration of antibiotic PS-6=25.8 pmoles/ml=8.63 μg/ml; optical density at 301 nm=0.366).

From this data, the Km value, 17.7 μM was calculated by the method of ShyunLong Yun and Clarence H. Suelter (Biochemica et Biophysica Acta, Vol. 480, pp. 1-13, 1977).

II Antibiotic PS-7

(1) Color
Colorless (2) Solubility
Soluble in water but practically insoluble in acetone (3) Decomposition point
No definite melting point was shown on the product, and it was gradually softened at 145°-150° C., shrinked in volume and looked solidified with color at 220° C. when it was measured by Kofler's method at a temperature-increasing rate of 1° C. per minute using a Micro Melting Point Test Apparatus, Type BY-1 (Yazawa Kagaku Kikaikogyo Co.).

Figure 4:
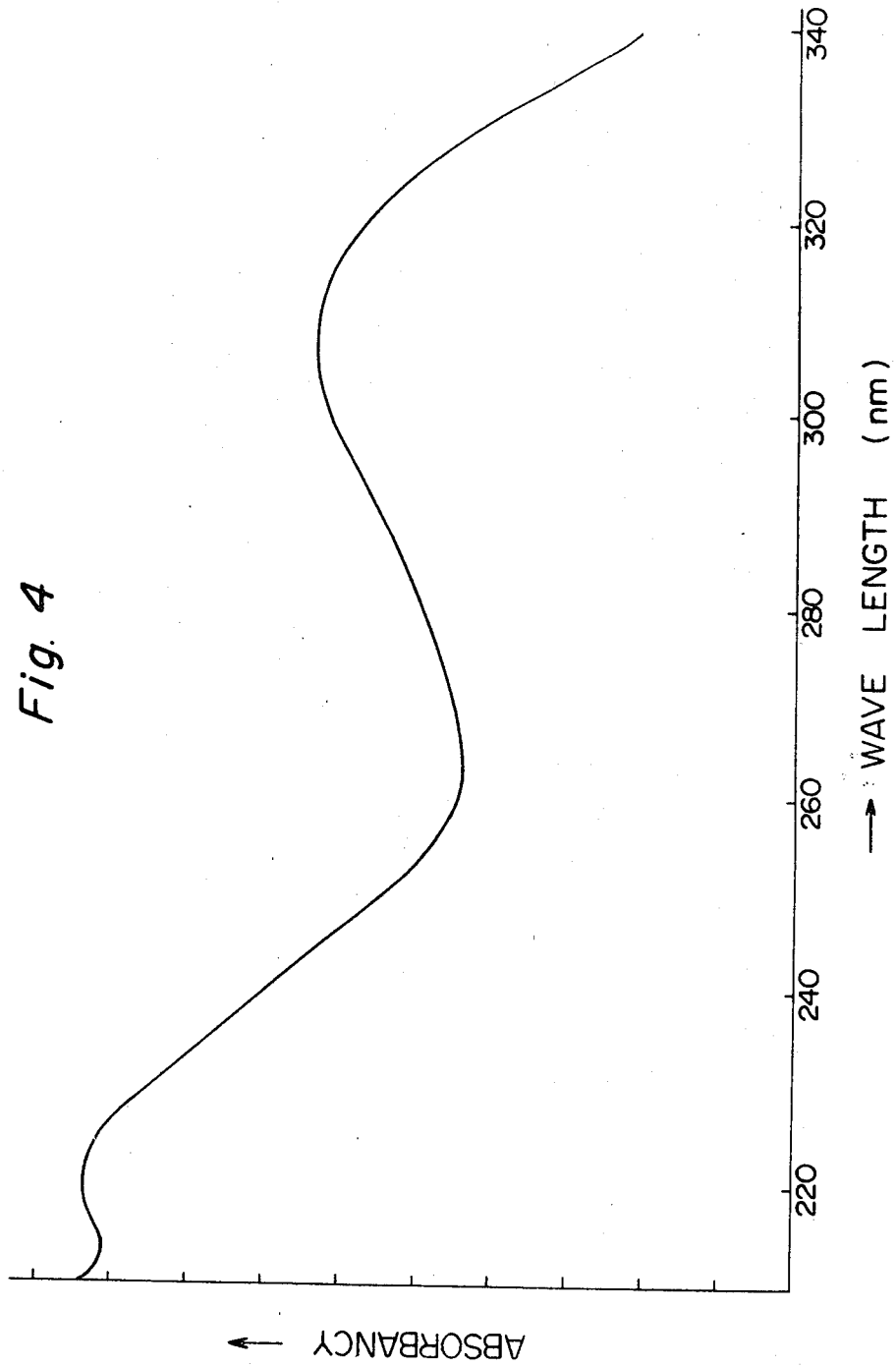
FIG. 4 shows the ultraviolet absorption spectrum of antibiotic PS-7 sodium salt.

(4) Ultraviolet absorption spectrum
FIG. 4 shows the ultraviolet absorption spectrum obtained by measuring with a solution containing 45 micrograms of sodium salt of the antibiotic PS-7 in 3 ml of M/100 phosphate buffer (pH 7.0) with a Shimadzu Digital Double Beam Spectrophotometer UV 210A. The characteristic values are as follows:

$\lambda_{max}^{H2O}$=about 220.0 nm and
$\lambda_{max}^{H2O}$=about 308.0 nm

About 95% of the absorbance at 308.0 nm was lost when an aqueous hydroxyl amine solution, pH 7.5, was added to a deionized water solution of the product and the concentrations of the product and hydroxylamine were adjusted to about 20 μg/ml and 10 mM, respectively and the mixture was incubated at 22° C. for 30 minutes.

Figure 5:
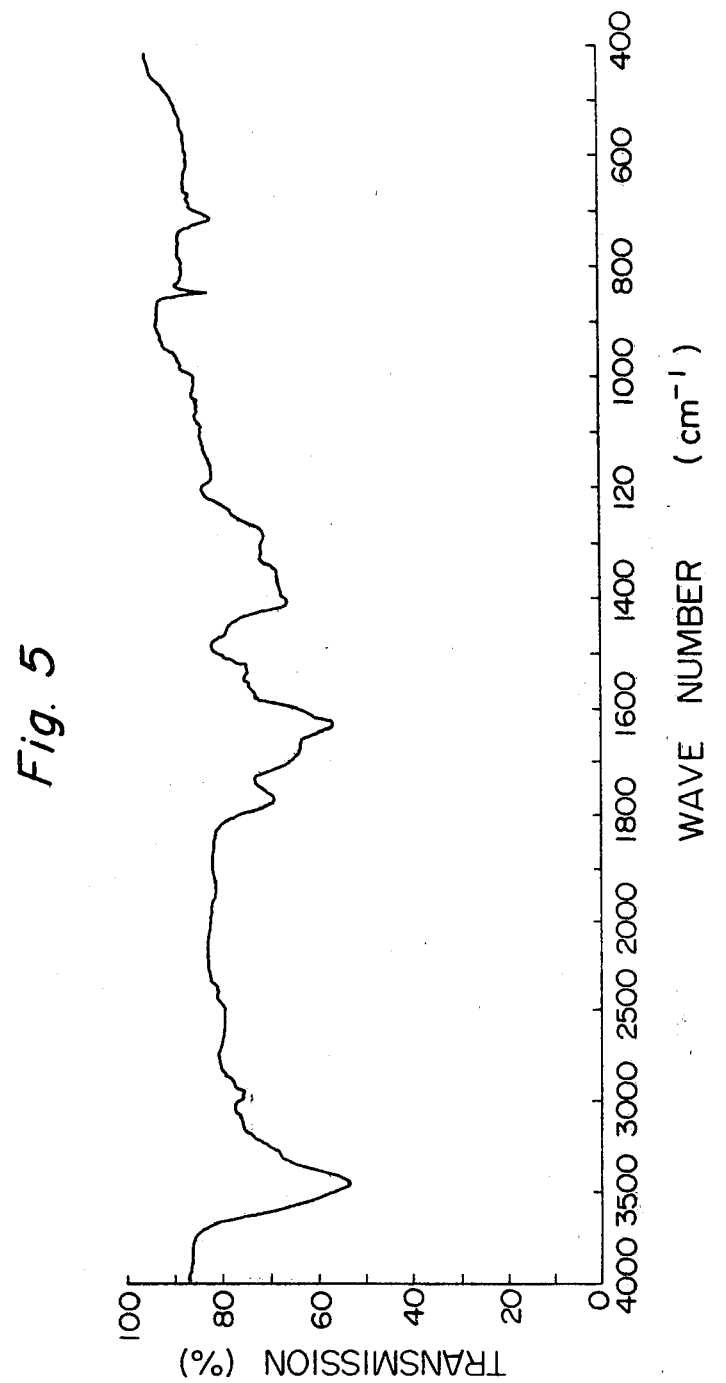
FIG. 5 shows the infrared absorption spectrum of antibiotic PS-7 sodium salt with KBr.

(5) Infrared absorption spectrum
FIG. 5 shows the infrared absorption spectrum measured with a KBr tablet using a Hitachi Infrared Spectrophotometer Type 215. The characteristic maximum absorption wave lengths were as follows:

(i) About 1760 cm$^{-1}$ (—CO— of β-lactam ring)
(ii) About 1670 cm$^{-1}$ (—CO— of amide)
(iii) About 1620 cm$^{-1}$ (—COO$^\ominus$ and —CH=CH—)

Figure 6:
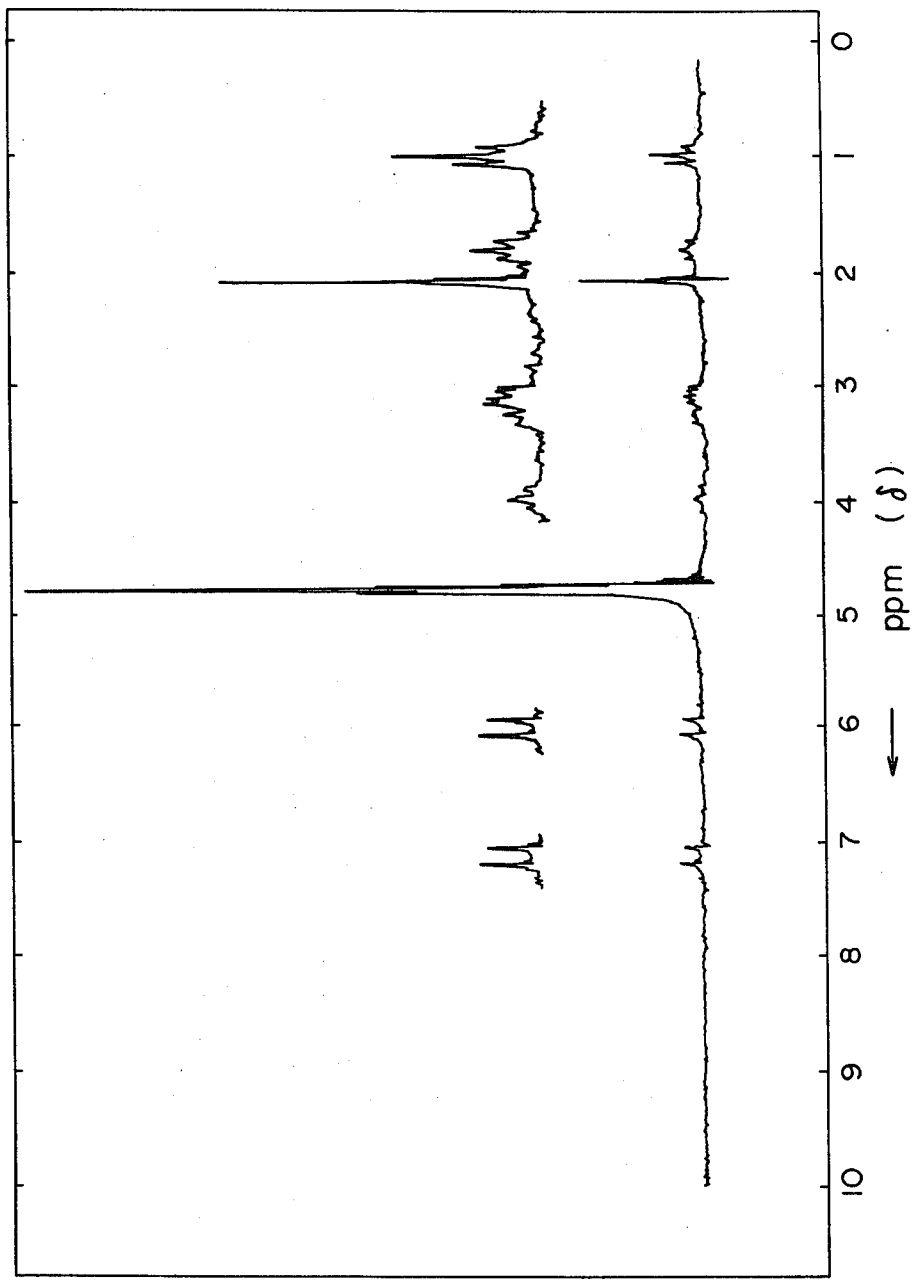
FIG. 6 shows the 100 MHz proton nuclear magentic resonance spectrum of antibiotic PS-7 sodium salt in heavy water.

(6) Proton nuclear magnetic resonance spectrum
FIG. 6 shows the 100 MHz proton nuclear magnetic resonance spectrum measured in heavy water with a Nihon Denshi JNM Type PS-100 apparatus. The appearent characteristic signals are as follows:

(i) A triplet with a center at about 0.96 ppm

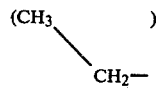

(ii) A multiplet with a center at about 1.72 ppm (—CH$_2$—CH$_3$)
(iii) A sharp singlet at about 2.05 ppm (CH$_3$—CO—)
(iv) A multiplet at about 2.96-3.38 ppm

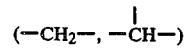

(v) A signal with a center at about 3.96 ppm

(vi) A pair of doublets centered at about 6.06 ppm and about 7.16 ppm (J=about 14 Hz) (—CH=CH—)

(7) Color reaction
Ehrlich reagent reaction: Positive
Iodine-chloroplatinic acid reaction: Positive
Ninhydrin reaction: Negative (8) Paper chromatography
The antibiotic PS-7 gave the following Rf values in descending paper chromatography on Toyo filter paper No. 50 (Toyo Roshi Co.) with the following solvent system:

Acetonitrile/Tirs/EDTA$^{(1)}$: Rf=0.41
Ethanol/Water (7/3): Rf=0.68

(9) Thin-layer chromatography (TLC)
The antibiotic PS-7 showed the following Rf values in TLC on a Chromagram sheet 13254 cellulose (No. 6065) (Fastman Kodak Co.) with the following solvent system:

n-Butanol/Ethanol/Water (4/1/5) (Upper layer): Rf=0.65
n-Propanol/Water (7/3): Rf=0.81
n-Butanol/Isopropanol/Water (7/7/6): Rf=0.71
Acetonitrile/Water (8/2): Rf=0.65

(10) High voltage paper electrophoresis
The following migration was observed with the antibiotic PS-7 in electrophoresis on Toyo filter paper No. 50 (Toyo Roshi Co.) with a buffer solution of the following pH value using a High-Voltage-Paper-Electrophoresis Apparatus (Savant Instruments Co., High voltage power supply HV 3000A, Electrophoresis vessel FP 18A).

The antibiotic PS-7 migrated toward the anode through a distance of 28 mm in a buffer solution consisting of 3.3 g of barbital, 25.5 g of sodium barbital and 3000 ml of water, pH 8.6 at a charge of 42 V/cm for 30 minutes.

The physico-chemical properties mentioned above shows that the antibiotic PS-7 obtained in this example has the following molecular structure:

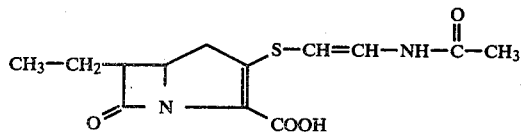

Furthermore the sodium salts of the antibiotic PS-7 obtained in this example were determined to have the following biological properties:

(1) Antimicrobial spectrum
Minimum inhibitory concentrations were determined on various pathogenic strains including resistant strains to the antibiotic PS-7 by the broth dilution method with a BRAIN HEART INFUSION BROTH "Eiken" (Eiken Chemical Co., Ltd.).

Sodium salt of the antibiotic PS-7 was dissolved and diluted with the BRAIN HEART INFUSION BROTH "Eiken" at a concentration between 5 μg/ml and 100 μg/ml. The solution was further diluted with the same medium to obtain a series of geometric concentrations. To the serial dilutions were added the seed cultures prepared by shaking culture of various test microorganisms shown in Tab. 5 in the BRAIN HEART INFUSION GROTH at 28° C. for 18 hours, the final cell count being about $1 \times 10^5$/ml. The cell growth was examined after incubation at 35° C. for 20 hours. The lowest concentration at which no cell growth was observed was the minimum inhibitory concentration of the antibiotic PS-7 on the test microorganism. As the control experiment, the known antibiotics Cephazolin and Cephoxitin were dissolved in the BRAIN HEART INFUSION BROTH, pH 7.0, at a concentration between 1 and 100 μg/ml, respectively, and diluted geometrically with the same medium to obtain serial dilutions. The minimum inhibitory concentrations on test strains were determined in the same manner as mentioned above. Table 7 shows the results. For the comparison, the results on the known antibiotics Cephazolin and Cefoxitin are also given in the same table.

TABLE 7

| Microorganism | Minimum inhibitory concentration | | |
|---|---|---|---|
| | Antibiotic PS-7 | Cephazolin | Cefoxitin |
| Staphylococcus aureus FDA 209P | <0.19 | 0.25 | 2.50 |
| Diplococcus pneumoniae Type III** | <0.19 | 0.125 | 2.50 |
| Alcaligenes faecalis B-326 | 0.78 | 6.25 | 1.56 |
| Citrobacter freundii E-9* | 3.13 | >100 | >100 |
| Enterobacter cloacae E-16* | 6.25 | >100 | >100 |

*β-Lactamase-producing strain
**Horse serum was contained in the medium at 10%.

(2) Potentiating and synergistic effect of the antimicrobial activity of β-lactam antibiotics against β-lactam-resistant microorganisms Cepholoridine was added to a 2.5-times diluted nutrient agar, pH 7.0 and the medium was inoculated with a β-lactam-producing strain that produceds β-lactamase. Ten ml of the medium was spread and solidified in a petri dish of 9 cm in diameter to prepare an assay plate. The antibiotic PS-7 was dissolved at a concentration of 50 μg/ml or 29 μg/ml, respectively. Each 20 μl of the solution and its 2- and 4-times diluted solutions was soaked in a pulp disc of 8 mm in diameter. To the surface of the above nutrient agar was placed the pulp disc and the size of the growth inhibitory zone around the disc was examined after incubation at 35° C. for 18 hours. As the control experiment, a similar experiment was carried out with a same medium without adding Cepholoridine. In addition, for the comparison, a similar experiment was also performed with a pulp disk soaked with 20 μl of 10,000 μg/ml Penicillin G or Cepholoridine solution in place of the antibiotic PS-7. The results are shown in Table 8.

TABLE 8

| β-Lactam-resistant strain | Disc | Diameter of inhibitory zone (mm) | |
|---|---|---|---|
| | | No addition | Cephaloridine-added |
| Proteus vulgaris P-5 | Antibiotic PS-7 | | |
| | x1 | 0.0 | 19.0 |
| | x2 | 0.0 | 15.0 |
| | x4 | 0.0 | 11.0 |
| | Penicillin G | 15.0 | 15.0 |
| | Cephaloridine | 12.0 | 12.0 |

The results show that, by addition of the antibiotic PS-7, evident enhancement of antimicrobial activity on β-lactam-resistant strains was observed in Penicillin G or Cepholoridine at such concentration as no antimicrobial activity was shown without the addition. No enhancement of antimicrobial activity was observed by addition of Penicillin G or Cephaloridine in place of the antibiotic PS-7.

(3) Activity in vivo

Activity of the antibiotic PS-7 obtained above was determined using mice infected with Staphylococcus aureus Smith at $5 \times 10^5$ cells a mouse intraperitoneally. Sodium salt of the antibiotic PS-7 was administered to the mice subcutaneously immediately after the infection. The $CD_{50}$ value of the compound was 7.5 mg/kg, respectively, in DDY male mice (Shizuoka).

(4) Toxicity

No acute toxicity was observed in DDY male mice (Shizuoka) to which sodium salt of the antibiotic PS-7 was administered intraperitoneally.

(5) Susceptibility to known β-lactamases (Characteristics of the antibiotic PS-7 as the enzymic substrate)

The behavior of the antibiotic PS-7 (sodium salt) against the induced-type penicillinase produced by Bacillus careus 569 (ATCC 27348) as the substrate was examined according to the following method:

(A) Reagents (1) Substrate:

Sodium salt of the antibiotic PS-7 was dissolved in 100 mM phosphate buffer solution (pH 6.8) at the indicated concentration.

(2) β-Lactamase:

The induced-type penicillinase of Bacillus cereus 569 (ATCC 27348) was induced by Ampicillin and partially purified by CM cellulose (Brown Co.) column chromatography. The enzyme preparation showed 14,800 units/ml of enzyme potency with potassium salt of Penicillin G as the substrate.

(B) Reaction and assay conditions

The solution of the antibiotic PS-7 that was served as the substrate was warmed at 30° C. A 3.0 ml-portion of the solution was poured in a quartz cuvette of 1 cm in optical path and the reaction was started by adding and mixing an indicated amount of enzyme. The reaction was carried out at 30° C. and a decrease in the substrate, antibiotic PS-7, was monitered by the absorbance at 308 nm.

A balance of absorbance at 308 nm was determined to be $\epsilon = 9720$ on the assumption that the $\epsilon$ value of the antibiotic PS-7 is 10,800 based on the decrease in the absorbance when pure preparation of the antibiotic PS-7 was completely decomposed by the enzyme above mentioned.

(C) Results

A reaction mixture containing 10 μl of the penicillinase preparation and 102 mμ moles of the antibiotic PS-7 (final concentration: 34 mμ moles/ml) in a total volumn of 3.0 ml was incubated under the conditions mentioned above and change of decreasing concentration of the antibiotic PS-7 was measured in relation to the incubation time.

Based on the results, Km value culculated according to Shyun-Long Yun and Clarence H. Sudlter's method (Biochemica et Biophysica Acta 480, 1-13 (1977)) was 13.0 μM in PS-7.

EXAMPLE 10

The trityl ester of antibiotic PS-6

25.9 mg of white freeze-dried preparation of antibiotic PS-6 sodium salt obtained according to the similar manner as described in Example 9 was dissolved in 5 ml of dimethyl-formamide and 20 μl of triethylamine and subsequently 50 mg of trityl chloride was added. After stirring at room temperature for 3 hours, the reaction mixture was diluted with 200 ml of benzene and washed 3 times with 70 ml of 0.1 M phosphate buffer solution (pH 6.8). After dehydration by adding 3 ml of saturated aqueous NaCl solution, benzene solution was dried by adding anhydrous sodium sulfate. Benzene was distilled under reduced pressure to give about 0.5 ml of benzene solution which was passed through a column (1.2×96.0 cm) of Bio-Beads S-X3 (Bio-Rad Laboratories). The column was developed with benzene. The active fractions thus obtained were combined and concentrated to dryness under reduced pressure. The obtained residue was dissolved in 0.5 ml of acetone and charged through a column (1.2×96.0 cm) of Sephadex LH-20 (Pharmacia Fine Chemicals AB) which had been swelled with acetone previously and the column was developed with acetone. The active fractions were combined and concentrated to dryness under reduced pressure to produce 23.7 mg of white powder. The recrystallization of this powder in a benzene-n-hexane mixture provided 17.5 mg of colorless crystalline powder of trityl ester of antibiotic PS-6.

This colorless crystalline powder had the following physico-chemical properties:

(1) Color

Colorless (2) Ultraviolet absorption spectrum

The ultraviolet absorption spectrum of the trityl ester of antibiotic PS-6 was recorded in a Hitachi Double Beam Spectrophotometer Model 200-20 (Hitachi, Ltd.) at a concentration of 100 μg/3 ml of methanol.

$\lambda_{max}^{MeOH} = 315.0$ nm (3) IR absorption spectrum

Figure 7:
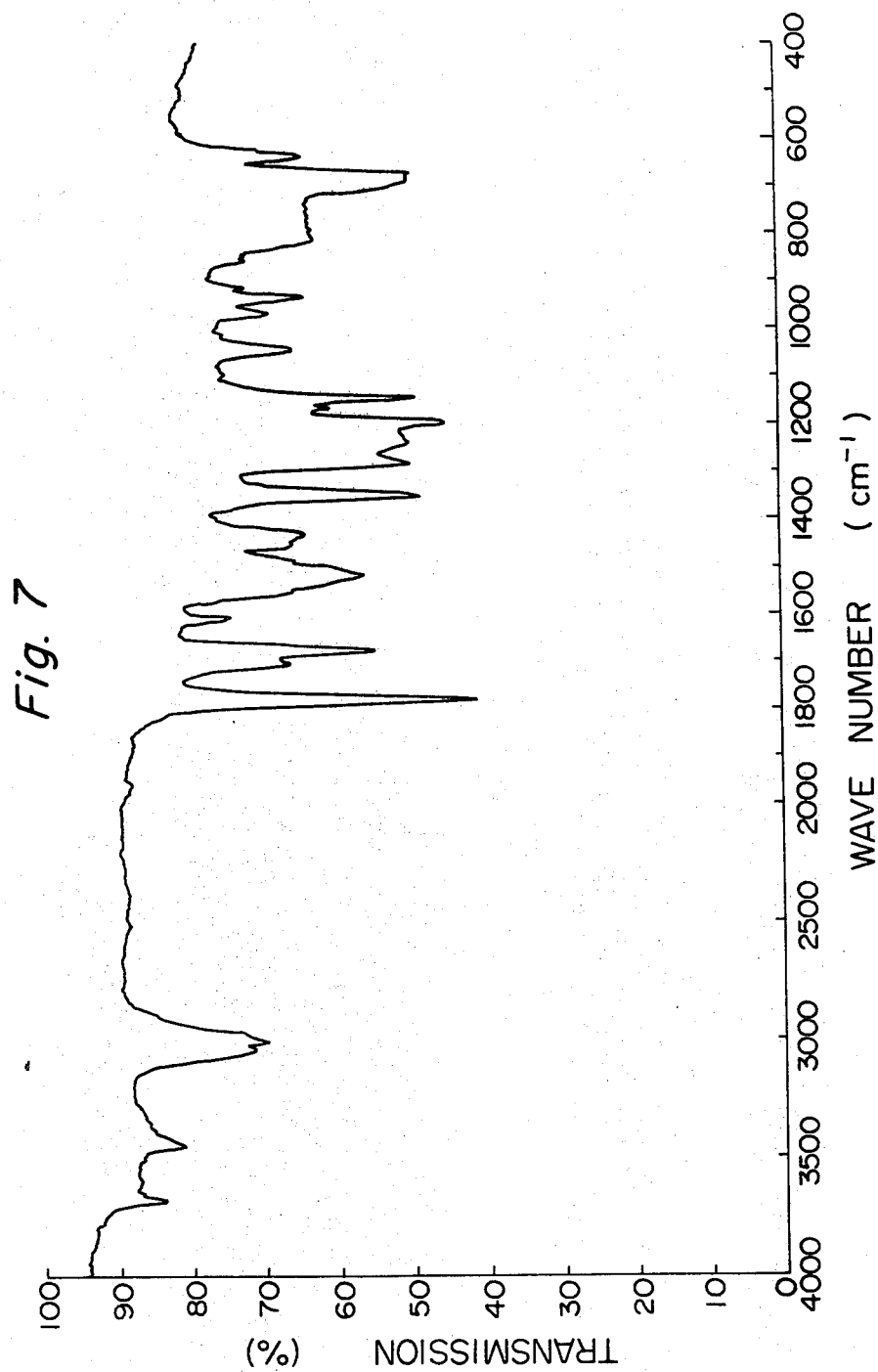
FIG. 7 shows the infrared absorption spectrum for the trityl ester of antibiotic PS-6 sodium salt.

200 μg of the trityl ester of antibiotic PS-6 was dissolved in 0.3 ml of $CHCl_3$, and its infrared absorption spectrum was measured by Hitachi Infrared Spectrophotometer (Model 260-30, Hitachi Limited) using a KBr fixed cell. The infrared absorption spectrum chart is shown in FIG. 7.

The following characteristic absorption maxima were located at the wave numbers indicated.

(i) ca. 1780 $cm^{-1}$ (—CO in the β-lactam ring)
(ii) ca. 1700 $cm^{-1}$ (—CO— in the amide bond)
(iii) ca. 1675 $cm^{-1}$ (—COO⊖ of the ester bond)
(4) Solubility The solubility of the trytilation product of antibiotic PS-6 was determined by dissolving under shaking, 5 mg each of the tritylation product of antibiotic PS-6 in 0.1 ml of each of the following solvents at 20° C. The results are as shown as below:

Substantially insoluble in water and n-hexane;
Highly soluble in benzene, ethyl acetate, chloroform, methanol, ethanol, acetone, dimethylformamide (DMF) and dimethylsulfoxide (DMSO).

(5) Color reaction

Ehrlich reagent reaction: positive
Iodine-chloroplatinic acid reaction: positive
Ninhydrin reaction: negative (6) Thin layer chromatography (TLC)

The trityl ester of antibiotic PS-6 provided the following $R_f$ values under the indicated conditions. The site of migration was revealed by bio-autography on *Comamonas terrigena* B-996

Silica gel TLC plate (Merck, DC-Fertigplatten Kiesel gel 60 $F_{254}$) was used, and prior to spotting, 2.5 μl of acetone solution containing 10% of dimethylformamide was spotted. The $R_f$ values were as follows:

Solvent system:

benzene/acetone (2/1): $R_f = 0.37$
benzene/ethylacetate (1/8): $R_f = 0.34$

From the molecular structure of antibiotic PS-6 and the above-specified physico-chemical properties of the antibiotic PS-6 trityl ester preparation, the following structure can be concluded as antibiotic PS-6 trityl ester:

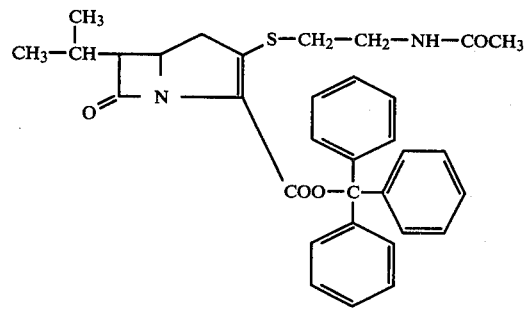

The biological properties of the trityl ester of antibiotic PS-6 are shown in the following:

(1) Antimicrobial spectrum

The MIC (minimum inhibitory concentration) values of the compound were determined on various pathogenic microorganisms including several resistant strains, utilizing the broth dilution method in BRAIN HEART INFUSION BROTH 'Eiken' (EIKEN CHEMICAL CO., LTD.).

More particularly, the trityl ester of antibiotic PS-6 was dissolved in a small amount of methanol and diluted as soon as possible in BRAIN HEART INFUSION BROTH 'Eiken' (pH 7.0) (EIKEN CHEMICAL CO., LTD.) until the concentration of the trityl ester of antibiotic PS-6 was in the range of 40 μg/ml to 20 μg/ml, and the concentration of methanol in the final solution did not exceed 10%. This solution was diluted in a two-fold geometric series. The microorganisms listed in Table 7 were cultivated for 18 hours at 28° C. in BRAIN HEART INFUSION BROTH 'Eiken' and inoculated to the above mentioned series of dilutions at a final inoculum size of 1×$10^5$ cells/ml. The results were read after incubation at 35° C. for 20 hours. The minimum inhibitory concentration (MIC) value means the lowest concentration unit of the tritylation product of antibiotic PS-6 where no growth of the corresponding microorganism was observed under the above-described conditions. As the control antibiotics, the solutions of ampicillin and cephaloridine were prepared in BRAIN HEART INFUSION BROTH 'Eiken' (pH 7.0) at a concentration of 100 μg/ml and treated same as the test compound of the present invention. Table 9 summarized the MIC values of the trityl ester of antibiotic PS-6 together with those of cephaloridine as the control antibiotics.

TABLE 9

| Microorganism | Minimum inhibitory concentration (μg/ml) | |
|---|---|---|
| | Trityl PS-6 | cephaloridine |
| *Staphylococcus aureus* FDA.209P | 0.33 | 0.04 |
| *Diplococcus pneumoniae* Type III** | 0.33 | 0.01 |
| *Streptococcus pyogenes* NY-5** | 0.33 | 0.01 |
| *Alcaligenes faecalis* B-326 | 1.34 | 3.13 |
| *Klebsiella pneumoniae* K-2* | 20.0 | 20.0 |
| *Citrobacter freundii* E-9* | 12.5 | >100 |
| *Proteus vulgaris* P-5* | 25.0 | >100 |
| *Enterobacter cloacae* E-16* | 25.0 | >100 |

Note:
*β-lactamase producing organism
**10% of horse blood is supplemented into the medium.

As apparent from the above-described Table, the trityl ester of antibiotic PS-6 exhibits a broad antimicrobial spectrum and particularly has a strong antibiotic activity on various beta-lactam-resistant (beta-lactamase-producing) strains of microorganisms.

(2) In vivo activity

The in vivo activity of the tritylation product of antibiotic PS-6 was measured in mice that were intraperitoneally infected with 5×10⁵ cells/mouse of *Staphylococcus aureus* Smith. The tritylation product of antibiotic PS-6 was subcutaneously injected just after infection. The 50% curative dose on male DDY mice (SHIZUOKA) was 5.5 mg/kg.

(3) Toxicity

In DDY male mice (Shizuoka), no acute toxicity of the antibiotic PS-6 trityl ester preparation was observed at the intraperitoneal dose of 500 mg/kg.

EXAMPLE 11

24.5 mg of a white freeze-dried preparation of antibiotic PS-7 sodium salt obtained in the same manner as described in Example 9 was dissolved in 5 ml of dimethylformamide and 20 μl of triethylamine, and subsequently 50 mg of trityl chloride was added. After stirring at room temperature for 3 hours, the reaction mixture was diluted with 200 ml of benzene and washed 3 times with 70 ml of 0.1 M phosphate buffer solution (pH 6.8). After dehydration by adding 3 ml of saturated aqueous NaCl solution, the benzene solution was dried by adding anhydrous sodium sulfate. Benzene was partially distilled under reduced pressure to give about 0.5 ml of the benzene solution which was then passed through a column (1.2×96.0 cm) of Bio-Beads S-X3 (Bio-Rad Laboratories). The column was developed with benzene. The active fractions thus obtained were combined and concentrated to dryness under reduced pressure. The obtained residue was dissolved in 0.5 ml of acetone and charged through a column (1.2×96.0 cm) of Sephadex LH-20 (Pharmacia Fine Chemicals AB) which had been swelled with acetone previously and the column was developed with acetone. The active fractions were combined and concentrated to dryness under reduced pressure to produce 20.5 mg of white powder. The recrystallization of this powder in a benzene-n-hexane mixture provided 15.5 mg of colorless crystalline powder of trityl ester of antibiotic PS-7. This colorless crystalline powder had the following physico-chemical properties:

(1) Color

Colorless (2) UV absorption spectrum

The ultraviolet absorption spectrum of the tritylation product of antibiotic PS-7 was recorded in a Hitachi Double Beam Spectrophotometer Model 200-20 (Hitachi, Ltd.) at a concentration of 100 μg/3 ml of methanol.

$\lambda_{max}^{MeOH} = 230.5$ nm, 321.5 nm (3) Solubility

The solubility of the tritylation product of antibiotic PS-7 was determined by dissolving under shaking, 5 mg each of tritylation product of antibiotic PS-7 in 0.1 ml of each of the following solvents at 20° C. The results are as shown below:

Substantially insoluble in water and n-hexane;
Highly soluble in benzene ethyl acetate, chloroform, methanol, ethanol, acetone, dimethylformamide (DMF) and dimethylsulfoxide (DMSO).

(4) Color reaction

Ehrlich reagent reaction: positive
Iodine-chloroplatinic acid reaction: positive
Ninhydrin reaction: negative (5) Thin layer chromatography (TLC)

The trityl ester of antibiotic PS-7 provided the following $R_f$ values under the indicated conditions. The site of migration was revealed by bio-autography on *Comamonas terrigena* B-996

Silica gel TLC plate (Merck, DC-Fertigplatten Kiesel gel 60 F₂₅₄) was used, and prior to spotting, 2.5 μl of acetone solution containing 10% of dimethylformamide was spotted. The $R_f$ values were as follows:

Solvent system:
benzene/acetone (2/1): $R_f = 0.51$
benzene/acetone (1/1): $R_f = 0.67$ From the molecular structure of antibiotic PS-7 and the above-specified physico-chemical properties of the antibiotic PS-7 trityl ester preparation, the following structure can be concluded as antibiotic PS-7 trityl ester:

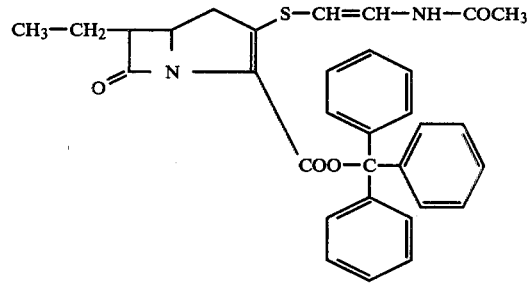

The biological properties of the trityl ester of antibiotic PS-7 are shown in the following:

(1) Antimicrobial spectrum

The MIC (minimum inhibitory concentration) values of the compound were determined on various pathogenic microorganisms including several resistant strains, utilizing the broth dilution method in BRAIN HEART INFUSION BROTH 'Eiken' (EIKEN CHEMICAL CO., LTD.).

More particularly, the trityl ester of antibiotic PS-7 was dissolved in a small amount of methanol and diluted as soon as posiible in BRAIN HEART INFUSION BROTH 'Eiken' (pH 7.0) (EIKEN CHEMICAL CO., LTD.) until the concentration of the trityl ester of antibiotic PS-6 was in the range of 40 μg/ml to 20 μg/ml, and the concentration of methanol in the final solution did not exceed 10%. This solution was diluted in a two-fold geometric series. The miroorganisms listed in Table 7 were cultivated for 18 hours at 28° C. in BRAIN HEART INFUSION BROTH 'Eiken' and inoculated to the above mentioned series of dilutions at a final inoculum size of $1 \times 10^5$ cells/ml. The results were read after incubation at 35° C. for 20 hours. The minimum inhibitory concentration (MIC) value means the lowest concentration unit of the tritylation product of antibiotic PS-7 where no growth of the corresponding microorganism was observed under the above-described conditions. As the control antibiotics, the solutions of ampicillin and cephaloridine were prepared in BRAIN HEART INFSSION BROTH 'Eiken' (pH 7.0) at a concentration of 100 μg/ml and treated same as the test compound of the present invention. Table 10 summarized the MIC values of the trityl ester of antibiotic PS-7 together with those of cephaloridine as the control antibiotics.

TABLE 10

| Microorganism | Minimum inhibitory concentration (μg/ml) | |
|---|---|---|
| | Trityl PS-7 | Cephaloridine |
| Staphylococcus aureus FDA.209P | 0.16 | 0.04 |
| Diplococcus pneumoniae Type III** | 0.16 | 0.01 |
| Streptococcus pyogenes NH-5** | 0.16 | 0.01 |
| Alcaligenes faecalis B-326 | 1.34 | 3.13 |
| Klebsiella pneumoniae K-2* | 10.0 | 20.0 |
| Citrobacter freundii E-9* | 6.25 | >100 |
| Proteus vulgaris P-5* | 25.0 | >100 |
| Enterobacter cloacae E-16* | 25.0 | >100 |

Note:
*β-lactamase producing organism
**10% of horse blood is supplemented into the medium.

As apparent from the above-described Table, the trityl ester of antibiotic PS-7 exhibits a broad antimicrobial spectrum and particularly has a strong antibiotic activity on various beta-lactam-resistant (beta-lactamase-producing) strains of microorganisms.

(2) In vivo activity

The in vivo activity of the tritylation product of antibiotic PS-6 was measured in mice that were intraperitoneally infected with $5 \times 10^5$ cells/mouse of *Staphylococcus aureus* Smith. The tritylation product of antibiotic PS-7 was subcutaneously injected just after infection. The 50% curative dose on make DDY mice (SHIZUOKA) was 4.5 mg/kg.

(3) Toxicity

In male DDY mice (Shizuoka), no acute toxicity of the antibiotic PS-7 trityl ester preparation was observed at the intraperitoneal dose of 500 mg/kg.

EXAMPLE 12

Antibiotic PS-6 methyl ester 2.0 mg of lyophilized preparation obtained in Example 9 was suspended in 1 ml of dry dimethylformamide (DMF), to which 20 μl of triethylamine and 50 μl of methyl iodide were added. After stirring the mixture for 2 hours at room temperature, about 20 μl of the mixture was sampled and dissolved in methanol, and applied to a Hitachi Recording Spectrophotometer Model EPS-3T (Hitachi Ltd.) for determining the increase of absorbancy at 315 nm to confirm the proceeding of the reaction. After the confirmation, all of the reaction mixture was poured into 20 ml of benzene and immediately washed twice with each 10 ml of 0.1 M phosphate buffer solution (pH 7.0). The benzene solution was dehydrated over anhydrous sodium sulfate and concentrated to 1 ml at 35° C. under reduced pressure. The concentrated solution was charged through a column (1.2×85 cm) of Bio-Beads S-X3 (Bio-Rad Laboratories) and developed with benzene. The eluate was developed on a thin layer chromatography (Kieselgel 60 $F_{254}$; benzene/acetone (1/1)), the eluate fractions were collected after identifying the fractions containing antibiotic PS-6 methyl ester by UV absorption spectrum. The fractions were concentrated to dryness under reduced pressure to obtain a colorless oily compound which was dissolved in 1 ml of acetone. The acetone solution was charged through a column (1.2×85 cm) of Sephadex LH-20 (Pharmacia Fine Chemicals AB) which previously had been filled with acetone and developed with acetone. After confirming the fractions containing antibiotic PS-6 methyl ester according to the method as described above, the fraction containing thereof were collected. The collected fraction was concentrated to dryness to obtain about 1.0 mg of white-oily antibiotic PS-6 methyl ester.

(1) Thin layer chromatography $R_f$=0.45 (Kieselgel 60 $F_{254}$ plate; benzene:acetone=1:1)

(2) Ultraviolet absorption maximum in methanol 316.6 nm (3) Molecular weight (High resolution mass spectrometry)

326.128683 (found)

Figure 8:
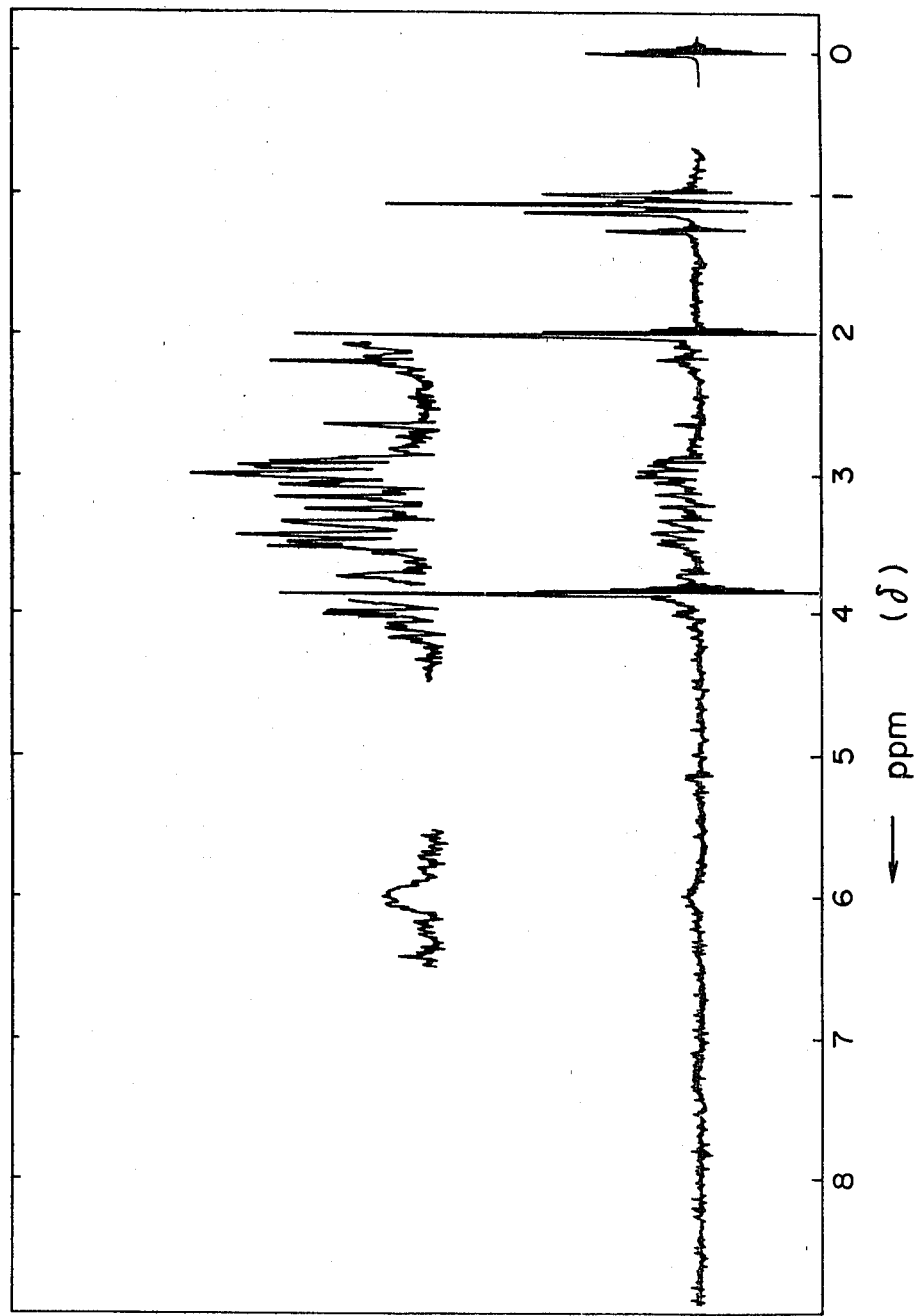
FIG. 8 is a proton nuclear magnetic resonance spectrum of the methyl ester of antibiotic PS-6.

326.130000: calculated for $C_{15}H_{22}N_2O_4S$ (4) Proton nuclear magnetic resonance The attached chart (FIG. 8) is the 100 $Mh_2$ proton magnetic resonance spectrum of the methyl ester of antibiotic PS-6 (solution of 2 mg of the methyl ester in 0.5 ml of deuterochloroform) in JEOL NMR spectrometer JNM PS-100 (Japan Electron Optics Laboratory Co., Ltd.). The following characteristic signals were confirmed:

(i) triplet* that has a center around 1.06 ppm

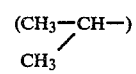

(ii) sharp singlet around 2.0 ppm (C$\underline{H}_3$—C—)
(iii) multiplet in the region of 2.6–3.6 ppm

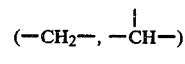

(iv) sharp singlet around 3.83 ppm

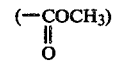

*A pair of doublets which overlap each other to make an apparent triplet having 6 protons.

As the molecular structure of antibiotic PS-6 methyl ester, the following can be considered from the earlier-described structure of antibiotic PS-6 and the above-specified physico-chemical data:

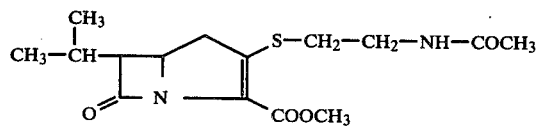

The procedure which was explained above in Example 11 was repeated with ethyl iodide, iso-propyl iodide, iso-butyl iodide, n-pentyl iodide or n-hexyl iodide instead of methyl iodide to obtain the following esters respectively:

antibiotic PS-6 ethyl ester
antibiotic PS-6 iso-propyl ester
antibiotic PS-6 iso-butyl ester
antibiotic PS-6 n-pentyl ester
antibiotic PS-6 n-hexyl ester The formation of these esters could be confirmed by thin layer chromatography, infrared absorption spectrometry, proton magnetic resonance spectrometry and mass spectrometry.

EXAMPLE 13

Antibiotic PS-7 methyl ester 2.0 mg of lyophilized preparation obtained in Example 9 was suspended in 1 ml of dry dimethylformamide (DMF), to which 20 μl of triethylamine and 50 μl of methyl iodide were added. After stirring the mixture for 2 hours at room temperature, about 20 μl of the mixture was sampled and dissolved in methanol, and applied to a Hitachi Recording Spectrophotometer Model EPS-3T (Hitachi Ltd.) for determining the increase of absorbancy at 32.15 nm to confirm the proceeding of the reaction. After the confirmation, all of the reaction mixture was poured into 20 ml of benzene and immediately washed twice with each 10 ml of 0.1 M phosphate buffer solution (pH 7.0). The benzene solution was dehydrated over anhydrous sodium sulfate and concentrated to 1 ml at 35° C. under reduced pressure. The concentrated solution was charged through a column (1.2×85 cm) of Bio-Beads S-X3 (Bio-Rad Laboratories) and developed with benzene. The eluate was developed on a thin layer chromatography (Kieselgel 60 $F_{254}$; benzene/acetone (2/1)), the eluate fractions were collected after identifying the fractions containing antibiotic PS-7 methyl ester by UV absorption spectrum. The fractions were concentrated to dryness under reduced pressure to obtain a colorless oily compound which was dissolved in 1 ml of acetone. The acetone solution was charged through a column (1.2×85 cm) of Sephadex LH-20 (Pharmacia Fine Chemicals AB) which previously had been filled with acetone and developed with acetone. After confirming the fractions containing antibiotic PS-7 methyl ester according to the method as described above, the fraction containing thereof were collected. The collected fraction was concentrated to dryness to obtain about 1.0 mg of white-oily antibiotic PS-7 methyl ester.

(1) Thin layer chromatography $R_f$=0.44 (Kieselgel 60 $F_{254}$ plate; benzene:acetone=2/1)

$R_f$=0.07 (Kieselgel 60 $F_{254}$ plate: chloroform:methanol=99:1)

(2) UV absorption maximum in methanol 230.5 nm, and 321.5 nm (3) Molecular weight (High resolution mass spectrometry)

310.37443 (found)

310.375760: calculated for $C_{14}H_{18}N_2O_4S$

As the molecular structure of antibiotic PS-7 methyl ester, the following can be considered from the earlier-described structure of antibiotic PS-7 and the above-specified physico-chemical data:

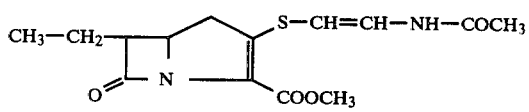

The procedure which was explained above in Example 11 was repeated with ethyl iodide, iso-propyl iodide, iso-butyl iodide, n-pentyl iodide or n-hexyl iodide instead of methyl iodide to obtain the following esters respectively:

antibiotic PS-7 ethyl ester
antibiotic PS-7 iso-propyl ester
antibiotic PS-7 iso-butyl ester
antibiotic PS-7 n-pentyl ester
antibiotic PS-7 n-hexyl ester The formation of these esters could be confirmed by thin layer chromatography, infrared absorption spectrometry, proton magnetic resonance spectrometry and mass spectrometry.

As explained before, composition containing at least one of antibiotics PS-6, PS-7 and the trityl derivatives thereof may be administered in various unit dosage forms such as solid or liquid orally ingestible dosage form. The said composition per unit dosage, whether solid or liquid, may contain the active material in an amount of 0.1–99%, preferably 10–60%. The amount of the active ingredient in the composition may change depending on the dosage form and the total weight of the composition, and usually is in the range of 10 mg to 1,000 mg, preferably 100 mg to 1,000 mg.

In parenteral administration, the unit dosage is usually the pure or highly purified at least one of antibiotics PS-6, PS-7 and the trityl derivatives thereof in sterile water solution or in the form of a soluble powder intended for solution.

Representative formulations containing sodium salt of at least one of antibiotics PS-6, PS-7 and trityl derivative thereof can be prepared by the following procedures:

EXAMPLE A: CAPSULES

| Component | Per capsule |
| --- | --- |
| Antibiotic PS-6 or PS-7 (sodium salt) | 100 mg |
| Lactose (J.P.) | a sufficient amount |
| Magnesium stearate | 1 mg |

The active compound and the diluents are mixed well in a mortar with a pestle to produce a uniform blend. Two hundred milligram of the blend is filled in a No. 3 hard gelatin capsule covered with enteric-coating.

EXAMPLE B: TABLETS

| Component | Per tablet |
| --- | --- |
| Antibiotic PS-6 or PS-7 (Sodium salt) | 200 mg |
| Lactose (J.P.) | 120 mg |
| Corn starch | 175 mg |
| Magnesium stearate | 5 mg |
| | 500 mg |

In the above composition, the active component is blended with lactose and a half amount of corn starch. The mixture is granulated with paste of 10% starch and screened. The balance of corn starch and magnesium stearate are added and the mixture is compressed into tablets, approximately 1 cm in diameter, each weighing 500 mg. The tablets thus obtained were covered first with enteric-coating and then with sugar coating.

EXAMPLE C: LYO FORM FOR INJECTION

| Component | Per vial |
| --- | --- |
| Antibiotic PS-6 or PS-7 | 25 mg |
| Sterile distilled water for injection (J.P.) | 2 ml |

The active component is dissolved in sterile distilled water for injection, filtered and sterilized. The soltuion is subdivided into sterile vials, and water is aseptically removed by lyophilization. The vials containing the sterile dry solid are aseptically sealed.

To restore for parenteral administration, 2 ml of sterile physiological saline (J.P.) is added to the content of a vial.

EXAMPLE D: TABLETS

| Component | Per tablet |
| --- | --- |
| Antibiotic PS-6 or PS-7 (sodium salt) | 20 mg |
| Cephaloridine | 180 mg |
| Lactose (J.P.) | 120 mg |
| Corn starch | 175 mg |
| Magnesium stearate | 5 mg |
| | 500 mg |

Antibiotic PS-6 or PS-7 and cephaloridine are mixed with the other ingredients and compressed into tablets as described in Example B. The tablets are covered first with an enteric coating and then with a sugar coating.

EXAMPLE E: TABLETS

| Component | Per tablet |
| --- | --- |
| Antibiotic PS-6 or PS-7 (Sodium salt) | 10 mg |
| Aminobenzylpenicillin | 190 mg |
| Lactose (J.P.) | 120 mg |
| Corn starch | 175 mg |
| Magnesium stearate | 5 mg |
| | 500 mg |

By the same method as described in Example B, the tablets containing antibiotic PS-6 or PS-7 (Sodium salt) and aminobenzylpenicillin are obtained.

EXAMPLE F: CAPSULES

| Component | Per capsule |
| --- | --- |
| Trityl ester of antibiotic PS-6 or PS-7 | 100 mg |
| Lactose | a sufficient quantity |
| Magnesium stearate | 1 mg |

The said active ingredient and diluents are well mixed to give a uniform blend. About 200 mg of each blend is filled in a No. 3 hard capsule and covered with enteric coating.

EXAMPLE G: TABLETS

| Component | Per tablet |
| --- | --- |
| Trityl ester of antibiotic PS-6 or PS-7 | 200 mg |
| Lactose (J.P.) | 120 mg |
| Corn starch | 175 mg |
| Magnesium stearate | 5 mg |
| | 500 mg |

In the above example, the active ingredient is blended with lactose and a half amount of corn starch in the indicated ratio. The mixture is granulated with paste of 10% starch and sieved. Magnesium stearate and the balance of corn starch are added and the mixture is compressed into tablets of 1 cm in diameter, each weighing 500 mg. The tablets are covered first with an enteric-coting and then with a sugar-coating.

EXAMPLE H: LYO FORM FOR INJECTION

| Component | Per vial |
| --- | --- |
| Trityl ester of antibiotic PS-6 or PS-7 | 25 mg |
| Sterile distilled water for injection (J.P.) | 2 ml |

The active component is dissolved in sterile distilled water for injection and sterilized by filtration. The solution is subdivided in vials and aseptically freeze-dried. The vials containing the sterile dry solid are aseptically sealed.

On injection, 2 ml of sterile 70% N-($\beta$-hydroxyethyl)-lactamide is added to the content of a vial.

EXAMPLE I: TABLETS

| Component | Per tablet |
| --- | --- |
| Trityl ester of antibiotic PS-6 or PS-7 | 20 mg |
| Cephaloridine | 180 mg |
| Lactose (J.P.) | 120 mg |
| Corn starch | 175 mg |
| Magnesium stearate | 5 mg |
| | 500 mg |

The trityl ester of antibiotic PS-6 or PS-7 and cephaloridine are mixed and then by the same method as described in Example G, compressed into tablets and coated.

EXAMPLE J: TABLETS

| Component | Per tablet |
|---|---|
| Trityl ester of antibiotic PS-6 or PS-7 | 20 mg |
| Aminobenzylpenicillin | 180 mg |
| Lactose (J.P.) | 120 mg |
| Corn starch | 175 mg |
| Magnesium stearate | 5 mg |
| | 500 mg |

The active ingredients (the trityl ester of antibiotic PS-6 or PS-7 and aminobenzylpenicillin) are mixed and processed by the same method as described in Example 1.

We claim:

1. A compound of the formula

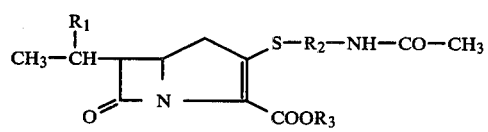

wherein $R_1$ is $CH_3$ and $R_2$ is $-CH_2-CH_2-$ or $R_1$ is H and $R_2$ is $-CH=CH-$; and $R_3$ represents hydrogen, lower alkyl or triphenylmethyl, or a salt of a compound of formula (I) wherein $R_3$ is hydrogen.

2. A compound of claim 1 wherein $R_3$ is hydrogen.

3. The compound of claim 1 wherein $R_1$ is $CH_3$, $R_2$ is $-CH_2-CH_2-$ and $R_3$ is triphenylmethyl.

4. The compound of claim 1 wherein $R_1$ is $CH_3$, $R_2$ is $-CH_2-CH_2-$ and $R_3$ is methyl.

5. A compound of claim 1 which is a pharmaceutically acceptable salt of a compound wherein $R_3$ is hydrogen.

6. A compound of the formula

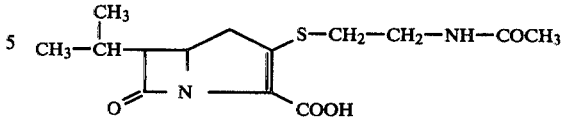

or a pharmaceutically acceptable salt thereof.

7. A compound of the formula

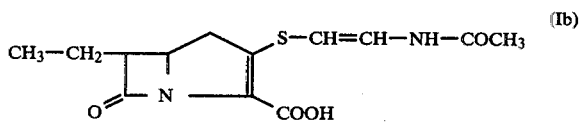

or a pharmaceutically acceptable salt thereof.

8. A pharmaceutical preparation having an antimicrobial activity containing an antimicrobially effective amount of a compound of the formula

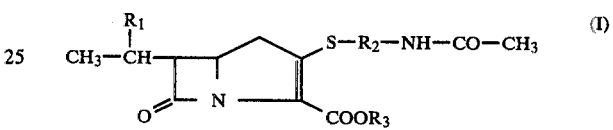

wherein $R_1$ is $CH_3$ and $R_2$ is $-CH_2-CH_2-$ or $R_1$ is H and $R_2$ is $-CH=CH-$; and $R_3$ represents hydrogen, lower alkyl or triphenylmethyl, or a pharmaceutically acceptable salt of a compound of formula (I) wherein $R_3$ is hydrogen and a pharmaceutically acceptable carrier therefor.

9. A method for combatting or preventing a bacterial infection in animals which comprises administering to the animals an antibiotically effective amount of a compound of the formula

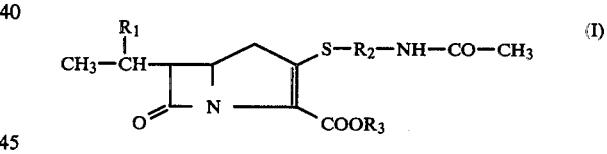

wherein $R_1$ is $CH_3$ and $R_2$ is $-CH_2-CH_2-$ or $R_1$ is H and $R_2$ is $-CH=CH-$; and $R_3$ represents hydrogen, lower alkyl or triphenylmethyl, or a pharmaceutically acceptable salt of a compound of formula (I) wherein $R_3$ is hydrogen.

* * * * *